United States Patent
Wannamaker et al.

(10) Patent No.: US 7,109,357 B2
(45) Date of Patent: Sep. 19, 2006

(54) PROCESS AND INTERMEDIATES FOR MAKING SUBSTITUTED ASPARTIC ACID ACETALS

(75) Inventors: Marion W. Wannamaker, Stow, MA (US); Cornelia Forster, Pelham, NH (US)

(73) Assignee: Vertex Pharmaceuticals Incorporated, Cambridge, MA (US)

( * ) Notice: Subject to any disclaimer, the term of this patent is extended or adjusted under 35 U.S.C. 154(b) by 0 days.

(21) Appl. No.: 10/229,981

(22) Filed: Aug. 28, 2002

(65) Prior Publication Data

US 2003/0119899 A1 Jun. 26, 2003

Related U.S. Application Data

(63) Continuation of application No. PCT/US01/12769, filed on Apr. 19, 2001.
(60) Provisional application No. 60/199,329, filed on Apr. 24, 2000.

(51) Int. Cl.
*C07D 307/56* (2006.01)

(52) U.S. Cl. .................................................. 549/313
(58) Field of Classification Search .................. 549/313
See application file for complete search history.

(56) References Cited

FOREIGN PATENT DOCUMENTS

| DD | 279 672 A | 6/1990 |
|----|-----------|--------|
| DD | 279 673 A | 6/1990 |
| EP | 0 071 500 | 2/1983 |
| WO | WO 99/03852 | 1/1999 |

OTHER PUBLICATIONS

Lakshmipathi, P., et al., "Efficient Conjugate Addition of Hydrogen Azide to Enoates," *Tetrahedron Letters*, 38(14):2551–2552 (1997).

Chu, C.K., et al., "An Efficient Total Synthesis of 3'–Azido–3'–Deoxythymidine (AZT) and 3'–Azido–2', 3'–Dideoxyuridine (AZDDU, CS–87) From D–Mannitol," *Tetrahedron Letters*, 29(42):5349–5352 (1988).

*Primary Examiner*—Amelia A. Owens
(74) *Attorney, Agent, or Firm*—Lisa A. Dixon; Vertex Pharmaceuticals Incorporated

(57) ABSTRACT

Disclosed herein is a method for making compounds that are useful as caspase inhibitor prodrugs of formula I:

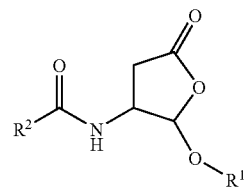

wherein $R^1$ is an optionally substituted group selected from an aliphatic group, aralkyl group, heterocyclylalkyl group or aryl group, and $R^2$ is preferably a $P_2$—$P_4$ moiety of a caspase inhibitor. Key intermediates include the azidolactones III and VIII:

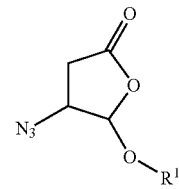

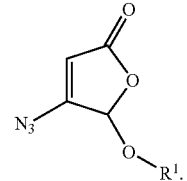

39 Claims, No Drawings

PROCESS AND INTERMEDIATES FOR MAKING SUBSTITUTED ASPARTIC ACID ACETALS

RELATED APPLICATIONS

This application is a CON of PCT/US01/12769 which claims benefit of 60/199,329 filed Apr. 24, 2000.

This application claims priority to U.S. Provisional Patent Application 60/199,329 filed Apr. 24, 2000.

FIELD OF THE INVENTION

This invention relates to a process for the synthesis of substituted aspartic acid acetals. The process is useful for preparing biologically active compounds, particularly certain caspase inhibitors, or prodrugs thereof, such as inhibitors of interleukin-1β converting enzyme ("ICE").

BACKGROUND OF THE INVENTION

Caspases are a family of cysteine protease enzymes that are key mediators in the signaling pathways for apoptosis and cell disassembly (Thornberry, *Chem. Biol.*, 1998, 5, R97–R103). Apoptosis, or programmed cell death, is a principal mechanism by which organisms eliminate unwanted cells. The deregulation of apoptosis, either excessive apoptosis or the failure to undergo it, has been implicated in a number of diseases such as cancer, acute inflammatory and autoimmune disorders, and certain neurodegenerative disorders (see generally *Science*, 1998, 281, 1283–1312; Ellis et al., *Ann. Rev. Cell. Biol.*, 1991, 7, 663). Caspase-1, the first identified caspase, is also known as interleukin-1β converting enzyme or "ICE." Caspase-1 converts precursor interleukin-1β ("pIL-1β") to the proinflammatory active form by specific cleavage of pIL-1β between Asp-116 and Ala-117. Besides caspase-1 there are also eleven other known human caspases which have been classified into families based on their biological function.

A number of useful caspase inhibitors has been reported that contain an aspartic acid aldehyde moiety, which will exist in equilibrium with its cyclic hemiacetal form as shown below:

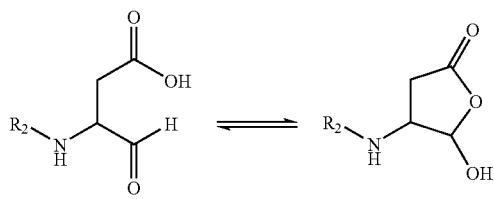

where $R_2$ represents the rest of the caspase inhibitor molecule. Based on the hemiacetal, orally available prodrugs of these inhibitors have been developed having the acetal structure 1, where $R_1$ is alkyl or aralkyl, as exemplified by 2. The ICE inhibitor 2 is a prodrug being developed as a treatment for rheumatoid arthritis (see U.S. Pat. No. 5,716,929).

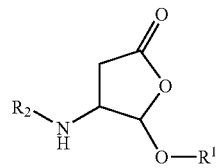

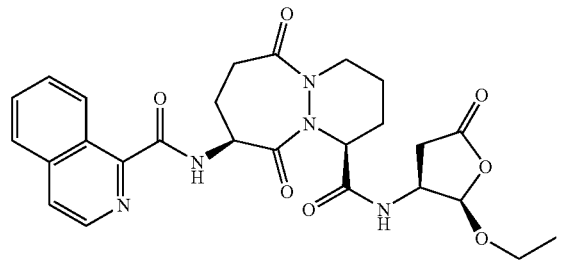

A process for the preparation of a peptidic caspase inhibitor prodrug of formula 1 where $R_1$ is benzyl and $R_2$ is the amino acid sequence Ac-Y-V-A has been described by Chapman et al. (*Bioorg. Med. Chem. Lett.* 1992, 2(6), 613). However, this route has significant disadvantages, especially if one wishes to obtain chiral compounds. For example, the process requires an expensive starting material and chromatographic separation of diastereomers (see discussion in PCT application WO/9903852).

More recently, a shorter process for the preparation of compounds of formula 1 where $R_1$ is ethyl has been described (PCT patent application WO/9903852). The process involves the conjugate addition of an aralkylamine to an alkoxyfuranone 3 to provide diastereomeric compounds 4 as shown below:

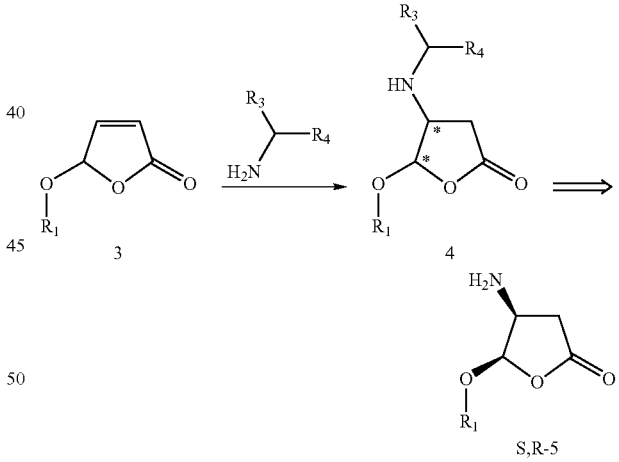

where $R_3$ is an alkyl group having one to four carbons and $R_4$ is an optionally substituted aryl group. The diastereomers of 4, or their addition salts, are reportedly separable by crystallization. The aralkyl group on the amine may then be removed by hydrogenolysis to liberate 5, a useful synthetic intermediate for preparing caspase inhibitors. One limitation to this approach is in the hydrogenolysis conditions used to remove $R_3R_4CH$— when $R_1$ is benzyl. Under such conditions, $R_1$ will also be removed.

It would be desirable to have a synthetic route to aspartic acetal caspase inhibitors, or prodrugs thereof, that is amenable to large-scale and overcomes the aforementioned shortcomings or otherwise improves upon the current methods.

DESCRIPTION OF THE INVENTION

This invention provides a process for making a compound of formula I:

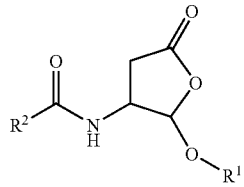

wherein $R^1$ is an optionally substituted group selected from an aliphatic group, aralkyl group, heterocyclylalkyl group, or aryl group, and $R^2$ is an organic radical. The process is particularly useful for obtaining compounds I where $R^2$ is a $P_2$—$P_4$ moiety of a caspase inhibitor, or portion thereof.

Certain compounds of formula I are prodrugs of caspase inhibitors, particularly ICE inhibitors. $R^2$ is preferably any moiety that, when attached to the rest of the molecule of formula I, provides such an inhibitor. Portions of $R^2$ are specifically referred to in the art as a $P_2$, $P_3$ or $P_4$ moiety or site. These $P_x$ terms are references to the amino acid sequence next to the aspartyl cleavage site of a particular caspase substrate. $P_1$ refers to the aspartyl residue of the substrate where caspase-induced cleavage occurs in the natural substrate. In the design of new, nonpeptidic caspase inhibitors, the $P_x$ designation is often retained to show which portion of the amino acid sequence has been replaced by the non-peptidic moiety. As used herein, the term "$P_2$—$P_4$" moiety refers to either the amino acid sequence described above or a chemical moiety known to replace such a sequence for the purpose of being a caspase substrate, and in particular an ICE substrate.

Examples of $P_2$—$P_4$ moieties that are non-peptidic are described in U.S. Pat. No. 5,919,790 (Allen et al.); U.S. Pat. No. 5,874,424 (Batchelor et al.); U.S. Pat. No. 5,847,135 (Bemis et al.); U.S. Pat. No. 5,843,904 (Bemis et al.); U.S. Pat. No. 5,756,466 (Bemis et al.); U.S. Pat. No. 5,716,929 (Bemis et al.); U.S. Pat. No. 5,656,627(Bemis et al.); WO 99/36426 (Warner-Lambert); Dolle et al., *J. Med. Chem.*, 40, 1941 (1997); WO 98/10778 (Idun); WO 98/11109 (Idun); WO 98/11129 (Idun)and WO 98/16502 (Warner Lambert), all of which are incorporated by reference.

One method of the present process for making I, referred to herein as Method A, comprises the steps of:

(a) providing a butenolactone of formula II:

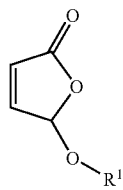

wherein $R^1$ is as described above;

(b) treating II with an azide $N_3$—Y, where Y is hydrogen, a silyl group, or a counterion, to form an azidolactone III:

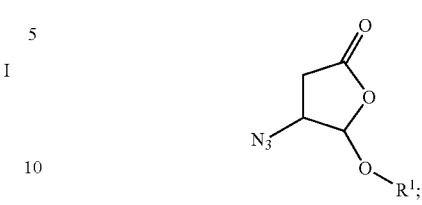

(c) converting III to an aminolactone IV or an iminophosphorane V:

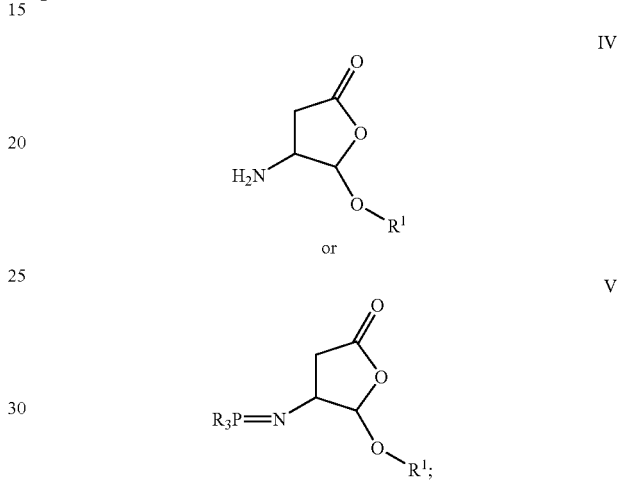

and (d) coupling IV or V with $R^2$COOH or reactive equivalent thereof, to form I. It will be understood that the $R^2$ group may be selected from any organic radical that is stable to conditions of the coupling reaction, such as those conditions described herein. Preferably $R^2$ is a $P_2$—, $P_2$—$P_3$—, or $P_2$—$P_3$—$P_4$— moiety.

As used herein, the following definitions shall apply unless otherwise indicated. The terms "lactone" and "furanone" may be used interchangeably as will be understood by one skilled in the art. The term "aliphatic" as used herein means straight chained, branched or cyclic $C_1$–$C_{12}$ hydrocarbons which are completely saturated or which contain one or more units of unsaturation. For example, suitable aliphatic groups include substituted or unsubstituted linear, branched or cyclic alkyl, alkenyl, alkynyl groups and hybrids thereof such as (cycloalkyl)alkyl, (cycloalkenyl)alkyl or (cycloalkyl)alkenyl. The term "alkyl" and "alkoxy" used alone or as part of a larger moiety refers to both straight and branched chains containing one to twelve carbon atoms. The terms "alkenyl" and "alkynyl" used alone or as part of a larger moiety shall include both straight and branched chains containing two to twelve carbon atoms. The term "aryl", used alone or as part of a larger moiety as in "aralkyl", refers to aromatic ring groups having five to fourteen members, such as phenyl, benzyl, 1-naphthyl, 2-naphthyl, 1-anthracyl and 2-anthracyl, and heterocyclic aromatic groups or heteroaryl groups such as 2-furanyl, 3-furanyl, N-imidazolyl, 2-imidazolyl, 4-imidazolyl, 5-imidazolyl, 3-isoxazolyl, 4-isoxazolyl, 5-isoxazolyl, a 1,3,4-oxadiazolyl, a 1,2,4-oxadiazolyl, 2-oxadiazolyl, 5-oxadiazolyl, 2-oxazolyl, 4-oxazolyl, 5-oxazolyl, 2-pyrrolyl, 3-pyrrolyl, 2-pyridyl, 3-pyridyl, 4-pyridyl, 2-pyrimidyl, 4-pyrimidyl, 5-pyrimidyl, 3-pyridazinyl, 2-thiadiazolyl, 5-thiadiazolyl, 2-thiazolyl, 4-thiazolyl, 5-thiazolyl, 5-tetrazolyl, 2-triazolyl, 5-triazolyl, 2-thienyl, or 3-thienyl. The term "aryl ring" also refers to rings that are optionally substituted. Aryl groups also include fused polycyclic aromatic ring systems in which a carbocyclic aromatic ring or heteroaryl ring is fused to one or more other rings. Examples include tetrahydronaphthyl, benzimidazolyl, benzothienyl, benzofuranyl, indolyl, quinolinyl, benzothiazolyl, benzooxazolyl, benzimidazolyl, isoquinolinyl, isoindolyl, acridinyl, benzoisoxazolyl, and the like. Also included within the scope of the term "aryl", as it is used herein, is a group in which one or more carbocyclic aromatic rings and/or heteroaryl rings are fused to a cycloalkyl or non-aromatic heterocyclic ring, for example, indanyl or tetrahydrobenzopyranyl. The term "heterocyclic group" refers to saturated and unsaturated monocyclic or polycyclic ring systems containing one or more heteroatoms and a ring size of three to eight such a piperidinyl, piperazinyl, tetrahydrofuranyl, pyrrolidinyl, tetrahydropyranyl, morpholinyl, and the like.

An aliphatic, alkyl, aryl, heterocyclic, or a carbocyclic group may contain one or more substituents. The substituents are selected from those that will be stable under the reaction conditions of the present process, as would be generally known to those skilled in the art. Examples of substituents include halogen, —R, —OR, —OH, protected OH (such as acyloxy), phenyl (Ph), substituted Ph, —OPh, substituted —OPh, —NO$_2$, —CN, —NHR, —N(R)$_2$, —NHCOR, —NHCONHR, —NRCONHR, —NHCON(R)$_2$, —NRCON(R)$_2$, —NRCOR, —NHCO$_2$R, —NRCO$_2$R, —CO$_2$R, —COR, —CONHR, —CON(R)$_2$, —S(O)$_2$R, —SONH$_2$, —S(O)R, —SO$_2$NHR, —SO$_2$N(R)$_2$, —NHS(O)$_2$R, —NRS(O)$_2$R, =O, =S, =NNHR, =NNR$_2$, =N—OR, =NNHCOR, =NNRCOR, =NNHCO$_2$R, =NNRCO$_2$R, =NNHSO$_2$R, =NNRSO$_2$R, or =NR where R is an optionally substituted aliphatic, aryl or aralkyl group.

A substitutable nitrogen on a heterocyclic ring may be optionally substituted. Suitable substituents on the nitrogen include R, COR, S(O)$_2$R, and CO$_2$R, where R is an aliphatic group or a substituted aliphatic group.

Unless otherwise stated, structures depicted herein are also meant to include all stereochemical forms of the structure; i.e., the R and S configurations for each asymmetric center. Therefore, single stereochemical isomers as well as enantiomeric and diastereomeric mixtures of the present compounds are within the scope of the invention. Unless otherwise stated, structures depicted herein are also meant to include compounds which differ only in the presence of one or more isotopically enriched atoms. For example, compounds having the present structures except for the replacement of a hydrogen by a deuterium or tritium, or the replacement of a carbon by a $^{13}$C- or $^{14}$C-enriched carbon are within the scope of this invention.

Butenolactone II is readily available and inexpensive. Preferred R$^1$ groups include methyl, ethyl, propyl, 2-propyl, butyl, pentyl, hexyl, 4-methylpentyl, 2-methylpropyl, cyclopentyl, cyclohexyl, cyclopentylmethyl, cyclohexylmethyl, phenylethyl, phenylpropyl, phenylbutyl, (d)-menthyl, (l)-menthyl, 1-adamantyl, 2-adamantyl, 1-indanyl, 2-indanyl, bornyl, 3-tetrahydrofuranyl, benzyl, α-methylbenzyl, 4-chlorobenzyl, 4-fluorobenzyl, 4-methylbenzyl, 4-(2-propyl)benzyl, and 4-trifluoromethylbenzyl. Most preferred R$^1$ groups include ethyl and benzyl.

The azidolactone III may be obtained by the conjugate or Michael addition of an N$_3$ group to II according to methods that are generally known in the art for analogous compounds (see S. J. Miller et al., 1999, *Org. Lett.*, 1(7), 1107). For example, III may be formed by adding II to a premixed solution of N$_3$—Y and an acid catalyst in a suitable solvent, followed by the addition of a Lewis base. The azide may be any nucleophilic azide known in the art to be suitable. Examples of such azides include alkali or alkaline earth salts of azide such as NaN$_3$ or LiN$_3$, tetralkylammonium azide, azidotrialkyl-, azidotriaryl-, azidoalkyldiaryl-, or azidodialkylarylsilanes such as trimethylsilylazide, triphenylsilylazide, or diphenylmethylsilylazide, or azidotrialkyltins such as azidotrimethyltin or azidotributyltin.

When N$_3$—Y is a trisubstituted silylazide such as trimethylsilylazide, the following conditions and reagents may be used. Suitable acid catalysts include carboxylic acids such as formic acid, acetic acid, propanoic acid, and benzoic acid, and halogenated carboxylic acids such as trifluoroacetic acid and trichloroacetic acid, and Lewis acids such as BF$_3$.OEt$_2$, aluminum trichloride, zinc chloride and titanium trichloride. Acetic acid and BF$_3$.OEt$_2$ are preferred acids. Suitable solvents include ethereal solvents such as tetrahydrofuran, DME, diethyl ether, methyl tert-butyl ketone, or dioxane; aromatic hydrocarbons such as benzene, toluene or xylene; halogenated hydrocarbons such as chloroform, carbon tetrachloride, dichloromethane, or dichloroethane. A preferred solvent is dichloromethane. The Lewis base need only be present in a catalytic amount. Suitable Lewis bases include aliphatic tertiary amines such as triethylamine, diisopropylamine, 1,8-diazabicyclo[5.4.0]undec-7-ene (DBU), 1,5-diazabicyclo[4.3.0]non-5-ene (DBN); heteroaromatic bases such as an N-alkylimidazole (which may be bound to a resin) or a pyridine. A preferred base is DBU. The reaction may be carried out at a temperature in the range of about 0° to 100° C., preferably between about 0° to 40° C., and most preferably between about 20° to 40° C. The concentration of II will be in the range of about 0.01M to 10M, preferably about 0.1 to 1.0M. The amounts of N$_3$—Y reactant such as trimethylsilylazide and Lewis acid will each generally be in the range of about 1.0 to 10 equivalents per equivalent of II.

The above conditions and reagents for converting II to III may vary depending on the nature of N$_3$—Y. When N$_3$—Y is an azide where the counterion is an alkaline earth metal such as lithium, sodium, barium or calcium, the following conditions and reagents may be used. The amount of azide will again be in the range of about 1.0 to 10.0 equivalents. The reaction temperature will be as described for trimethylsilylazide. Suitable acids include formic acid, acetic acid, benzoic acid and buffered acids such as tetrabutylammonium bisulfate, ammonium chloride, ammonium acetate, and ammonium formate. Preferred acids are acetic acid, tetrabutylammonium bisulfate, and ammonium chloride. The amount of acid will generally be in the range of about 1.0 to about 10.0 equivalents. Suitable solvents include nonprotic organic solvents such as acetone, N-methylpyrrolidone, methyl ethylketone, tetrahydrofuran (THF), dioxane, dimethoxyethane (DME), dimethylformamide (DMF) and the halogenated hydrocarbons described above.

When N$_3$—Y is HN$_3$, it is preferred that an excess of azide be used, generally about 5 to 25 equivalents of azide per equivalent of butenolactone II (see Lakschmipathi et al., 1997, *Tetrahedron Lett.*, 38(14), 2551). Only a catalytic amount of the base is required, generally in the range of about 0.01 to 0.25 equivalents, preferentially at least about 0.10 equivalents. Suitable bases include tertiary amine bases such as triethylamine, diisopropylamine, DBU, DBN or aromatic N-heterocycles such as pyridine, alkylpyridines and N-alkylimidazole (which may be resin bound), preferably triethylamine. Suitable solvents include aromatic hydrocarbons such as benzene, toluene or xylene, preferably toluene. The reaction temperature will generally be in the range of about 20° C. to about 110° C., preferably about 70° C. to about 90° C.

When $N_3$—Y is $Et_2AlN_3$, it is preferred to use about 1.0 to 3.0 equivalents of the azide per equivalent of butenolactone II. (Chung, et al., 1998, *Bull. Korean Chem. Soc.*, 9, 269) Suitable solvents include aprotic organic solvents such as diethyl ether, methyl tert-butyl ether, dioxane, tetrahydrofuran, hexane, benzene, and toluene which is a preferred solvent. The reaction temperature will be in the range of about –20° C. to about 40° C., preferably about 20° C. to about 40° C.

Azidolactone III may be converted to the corresponding aminolactone IV by hydrogenation or by a reaction with triphenylphosphine. Hydrogenation is more suitable when $R^1$ is a group that is stable to the hydrogenation conditions such as an alkyl group. Standard hydrogenation conditions may be used, such as using hydrogen gas at 1–4 atmospheres of pressure. Alternatively, the hydrogen may be generated in situ by known methods, such as from ammonium formate under phase transfer conditions.

Azidolactones III containing benzylic and other $R^1$ groups that are not stable to hydrogenation may be reduced to aminolactone IV with triphenylphosphine via the known Staudinger reaction. Similar reducing reagents include trimethyl-, triethyl-, or tributylphosphine, or an alkyl diphenylphosphinite such as methyl- or ethyldiphenylphosphinite. For this reduction, suitable solvents include aqueous organic solvents such as THF, dioxane, acetonitrile, acetone, and DMF containing about 1% to 50% water, preferably about 5% to 10% water. A preferred organic solvent is THF. The reaction temperature may be in the range of about 0° C. to about 60° C., preferably between about 20° C. to about 40° C.

Alternatively, the azidolactone III may be treated with triphenylphosphine or a similar reducing agent under anhydrous conditions to provide the iminophosphorane V, which is a useful intermediate:

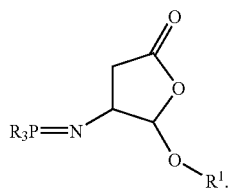

V

Therefore, one embodiment of Method A proceeds through intermediate V and another embodiment of Method A proceeds through intermediate IV.

The aminolactone IV, obtained as described above, may be used with or without isolation from the reaction mixture. The desired caspase inhibitor prodrug I is derived from IV by attaching the appropriate $P_2$, $P_2$—$P_3$, or $P_2$—$P_4$ moiety. A coupling of IV with such a moiety may be carried out using the corresponding carboxylic acid, or reactive equivalent thereof, under standard amide bond-forming or coupling conditions. A typical coupling reaction includes a suitable solvent, IV in a concentration ranging from about 0.01 to 10M, preferably about 0.1 to 1.0M, the requisite carboxylic acid, a base and a peptide coupling reagent.

If IV is used without isolation, the coupling may be carried out in situ in the solvent of the reaction mixture used in the preparation of IV, or in a different solvent. To this reaction mixture, the requisite carboxylic acid may be added and the reaction maintained at a temperature in the range of about 0° to 100° C., preferably between about 20° to 40° C. The base and peptide coupling reagent are then added to the mixture, which is maintained at a temperature in the range of about 0° to 60° C., preferably between about 20° to 40° C. The base is typically a tertiary amine base, such as triethylamine, diisopropylethylamine, N-methylmorpholine, DBU, DBN, N-methylimidazole, preferably triethylamine or diisopropylethylamine. The amount of base used is generally up to about 20 equivalents per equivalent of IV, preferably at least about 3 equivalents of base. Examples of peptide coupling reagents include DCC (dicyclohexylcarbodiimide), DIC (diisopropylcarbodiimide), di-p-toluoylcarbodiimide, BDP (1-benzotriazole diethylphosphate-1-cyclohexyl-3-(2-morpholinylethyl)carbodiimide), EDC (1-(3-dimethylaminopropyl-3-ethyl-carbodiimide hydrochloride), cyanuric fluoride, cyanuric chloride, TFFH (tetramethyl fluoroformamidinium hexafluorophosphate), DPPA (diphenylphosphorazidate), BOP (benzotriazol-1-yloxytris (dimethylamino)phosphonium hexafluorophosphate), HBTU (O-benzotriazol-1-yl-N,N,N',N'-tetramethyluronium hexafluorophosphate), TBTU (O-benzotriazol-1-yl-N,N,N',N'-tetramethyluronium tetrafluoroborate), TSTU (O-(N-succinimidyl)-N,N,N',N'-tetramethyluronium tetrafluoroborate), HATU (N-[(dimethylamino)-1-H-1,2,3-triazolo[4,5,6]-pyridin-1-ylmethylene]-N-methylmethanaminium hexafluorophosphate N-oxide), BOP-Cl (bis(2-oxo-3-oxazolidinyl)phosphinic chloride), PyBOP ((1-H-1,2,3-benzotriazol-1-yloxy)-tris(pyrrolidino) phosphonium tetrafluorophopsphate), BrOP (bromotris (dimethylamino)phosphonium hexafluorophosphate), DEPBT (3-(diethoxyphosphoryloxy)-1,2,3-benzotriazin-4 (3H)-one) PyBrOP (bromotris(pyrrolidino)phosphonium hexafluorophosphate). EDC, HOAT, BOP-Cl and PyBrOP are preferred peptide coupling reagents. The amount of peptide coupling reagent is in the range of about 1.0 to about 10.0 equivalents. Optional reagents that may be used in the amide bond-forming reaction include DMAP (4-dimethylaminopyridine) or active ester reagents, such as HOBT (1-hydroxybenzotriazole), HOAT (hydroxyazabenzotriazole), HOSu (hydroxysuccinimide), HONB (endo-N-hydroxy-5-norbornene-2,3-dicarboxamide), in amounts ranging from about 1.0 to about 10.0 equivalents.

Alternatively, one may treat either IV or V with a reactive equivalent of the $R^2COOH$ carboxylic acid, such as $P_2$—, $P_2$—$P_3$—, or $P_2$—$P_3$—$P_4$—C(=O)X, where C(=O)X is a group that is more reactive than COOH in the coupling reaction. Examples of —C(=O)X groups include groups where X is Cl, F, OC(=O)R (R=aliphatic or aryl), SH, SR, SAr, or SeAr. When V is the intermediate, rather than IV, it is preferred that the acid fluoride (X is F) be used in the coupling reaction. Suitable conditions for using these reactive equivalents are known in the art.

A number of chemical groups are known that may be used as the $P_3$—$P_2$— portion of the ICE or caspase inhibitor prodrug. Examples of such $P_3$—$P_2$— groups are shown in Table 1 as part of a $P_4$—$P_3$—$P_2$— moiety.

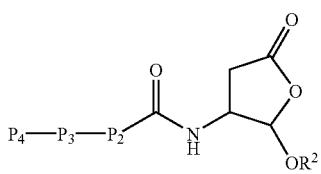

TABLE 1

P₄—P₃—P₂— Groups

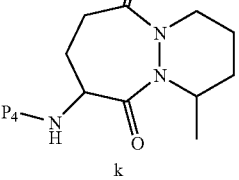

TABLE 1-continued

P₄—P₃—P₂— Groups

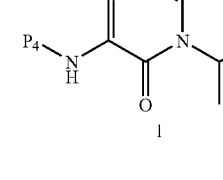

where n is zero to three; AA refers to an amino acid side chain; X is N, O, S, SO, SO₂, CHF, CF₂, C(R³)₂, C=O, or C=NOR; A is O, S or H₂; Y is N or CH; R is hydrogen, $C_{1-12}$ alkyl group, aryl group, or heteroaryl group, the R groups being optionally substituted with one or halogen; $R^3$ is an alkyl having one to six carbons; and $R^5$ is hydrogen, halo, alkyl, alkoxy, haloalkyl, haloalkoxy, amino, phenyl, phenoxy, hydroxy, alkoxycarbonyl, carboxyl, alkylcarbonyl, alkylsulfonyl, alkylsulfoxyl, alkylcarbonylamino, alkylcarbonylalkylamino, alkylamino, dialkylamino, aminosulfonyl, or cyano; and $R^6$ and $R^7$ are independently selected from $R^3$, aryl, heteroaryl, ($C_{1-12}$ alkyl)aryl, ($C_{1-12}$) benzocycloalkyl, or ($C_{1-12}$ alkyl)heteroaryl.

Preferred P₄—P₃—P₂— groups are shown in Table 2.

TABLE 2

Preferred P₄—P₃—P₂— Groups

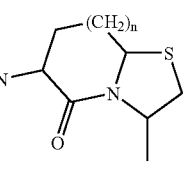

TABLE 2-continued
Preferred P4—P3—P2— Groups
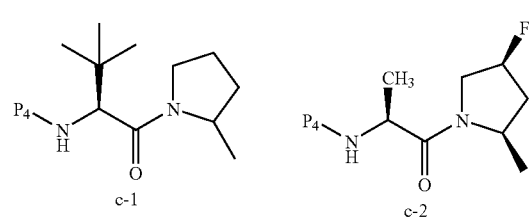
c-1    c-2
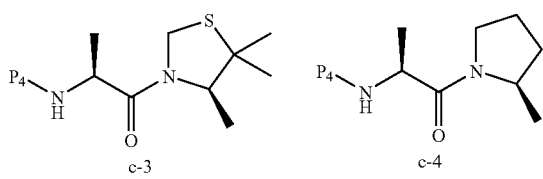
c-3    c-4
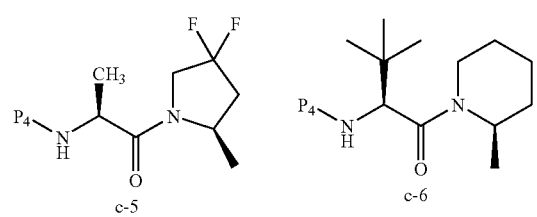
c-5    c-6
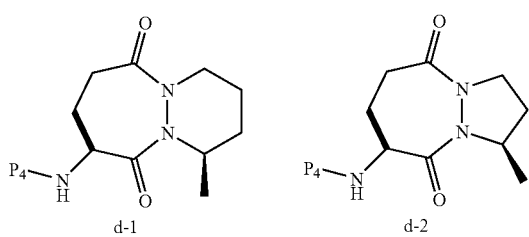
d-1    d-2
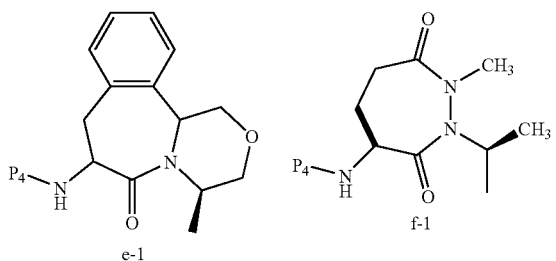
e-1    f-1
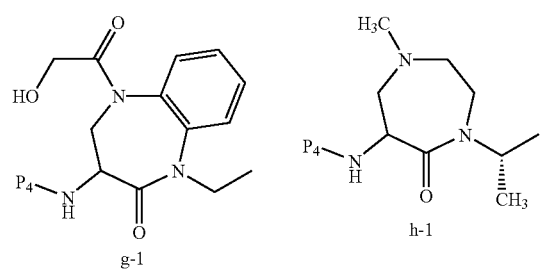
g-1    h-1
TABLE 2-continued
Preferred P4—P3—P2— Groups
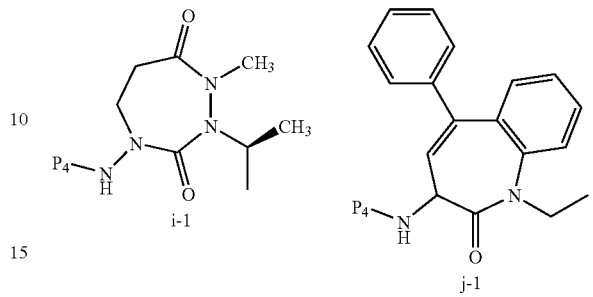
i-1    j-1
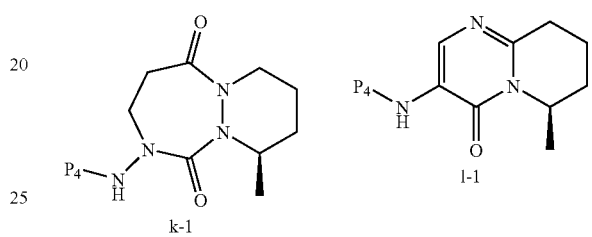
k-1    l-1
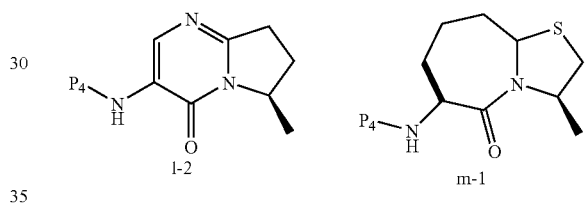
l-2    m-1
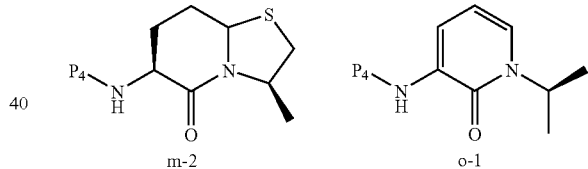
m-2    o-1
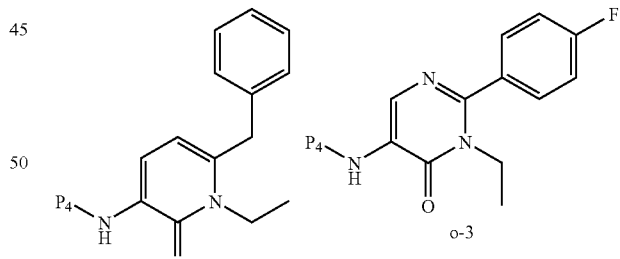
o-2    o-3
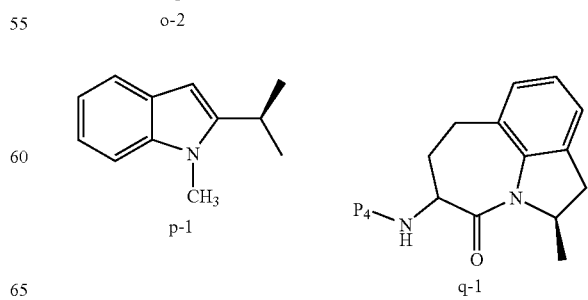
p-1    q-1

TABLE 2-continued
Preferred P₄—P₃—P₂— Groups
r-1
r-2
n-1
where $R^6$ is an optionally substituted benzyl as described below or 2-indanyl, and the $P_4$ moiety is represented by R—T—, where R—T is R—CO, ROC=O, RNHC=O, RC(O)C=O, or RSO₂. Preferred R groups of $P_4$ are shown in Table 3.
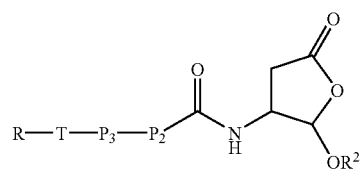
TABLE 3
Preferred R Groups of P₄
100, 101, 102, 103
104, 105, 106
107, 108
TABLE 3-continued
Preferred R Groups of P₄
109, 110, 111
112, 113
114, 115
116, 117, 119
120, 121
122, 123
124, 125
126, 127

TABLE 3-continued

Preferred R Groups of P₄

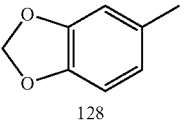

Most preferably, R—T— is R—CO where R is 1-naphthyl, 2-naphthyl, 1-isoquinolinyl, or

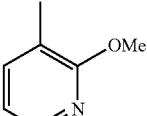

where positions 3 and 5 of R are independently and optionally substituted by halogen, preferably chloro, or C₁₋₃ alkyl, and position 4 is optionally substituted by amino, acetamido, hydroxy or methoxy.

The most preferred P₄—P₃—P₂— groups are shown in Table 4.

TABLE 4

Most Preferred P₄—P₃—P₂— Groups

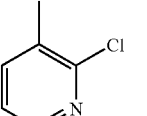

a-1a

TABLE 4-continued

Most Preferred P$_4$—P$_3$—P$_2$— Groups

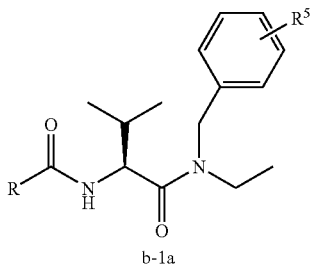
b-1a

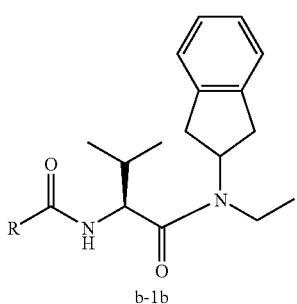
b-1b

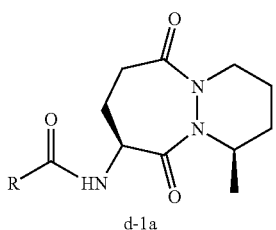
d-1a

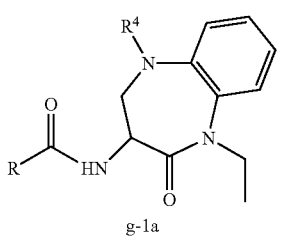
g-1a

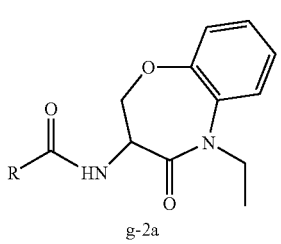
g-2a

TABLE 4-continued

Most Preferred P$_4$—P$_3$—P$_2$— Groups

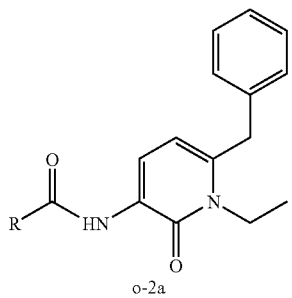
o-2a

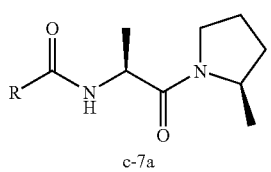
c-7a

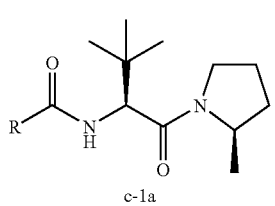
c-1a

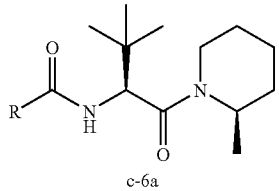
c-6a where R is, referring to Table 3, one of the following groups: 100, 105, 107, 108, 114, 117, 119, 126, 136, 139, 140, and 141.

In attaching the P$_4$—P$_3$—P$_2$ moiety, or portion thereof, the moiety may be attached in one piece as described above or subunits of the moiety may be added in a sequential manner. For example, Boc-protected proline may be coupled to IV to provide VI.

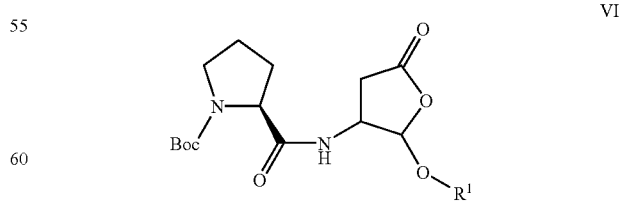

VI

After removal of the Boc group, a P$_3$ or P$_3$—P$_4$ moiety may be attached by alkylation or acylation of the proline nitrogen.

(4R, 5R)-IIIa

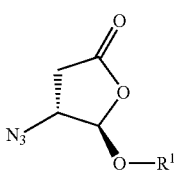

(4S, 5S)-IIIb

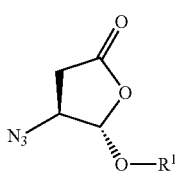

Ia

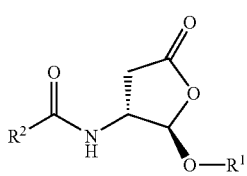

Ib

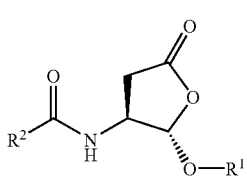

Ic

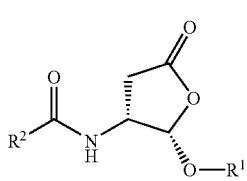

Id

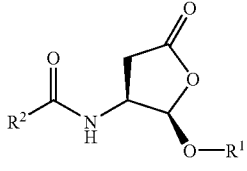

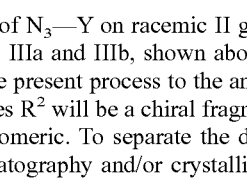

The reaction of $N_3$—Y on racemic II generally produces the anti isomers IIIa and IIIb, shown above. These may be converted by the present process to the anti products Ia and Ib. In many cases $R^2$ will be a chiral fragment and Ia and Ib will be diastereomeric. To separate the diastereomers, one may use chromatography and/or crystallization, depending on the nature of $R^1$ and $R^2$. Epimerization of either Ia or Ib provides the syn isomers Ic or Id, respectively. The epimerization reaction is performed in the presence of a protic acid or Lewis acid (French patent application 97/08932). Suitable Lewis acids include ferric chloride, titanium tetrachloride, boron trichloride, boron trifluoride and tin tetrachloride and suitable protic acids include organic acids such as methanesulfonic acid, trifluoroacetic acid and para toluenesulfonic acid and mineral acids such as hydrochloric acid and sulfuric acid.

Another method of the present process for making a compound I proceeds through the butenolactone VII where X is chloro, bromo or iodo:

VII

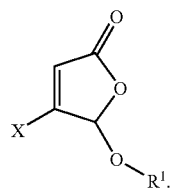

A preferred starting butenolactone VII is the bromofuranone (X=Br), which may be obtained according to Escobar et al., *An. Quim.*, 1971, 67, 43. This process, referred to herein as Method B, comprises the steps of:

(a) providing a butenolactone VII:

VII

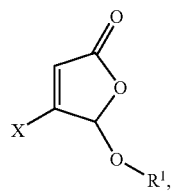

wherein $R^1$ is as described above, and X is chloro, bromo or iodo;

(b) treating VII with an azide $N_3$—Y, where Y is a silyl group or a counterion, to form an azidobutenolactone VIII:

VIII

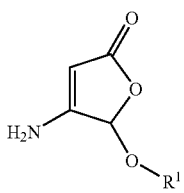

(c) converting VIII to an aminobutenolactone IX or iminophosphorane XI:

IX

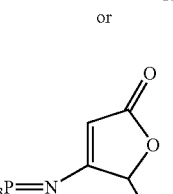

or

XI

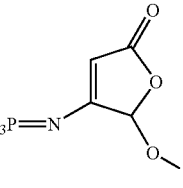

(d) coupling either IX or XI with $R^2COOH$, or a reactive equivalent thereof, to form X:

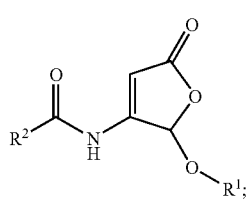

and
(e) reducing the furanone ring double bond in X to provide I. $R^2COOH$ is an organic radical, preferably a $P_2$—, $P_2$—$P_3$—, or $P_2$—$P_4$ carboxylic acid.

It will be apparent that steps b–d of the above Method B process are analogous to those described earlier with respect to Method A, and may be carried out in a similar manner.

Also within the scope of this inventions another embodiment of the coupling reaction of amine IX to form I proceeds by acylation of the anion of IX using a reactive equivalent of the carboxylic acid, such as $P_2$—, $P_2$—$P_3$—, or $P_2$—$P_3$—$P_4$—C(=O)X, where C(=O)X is as described above. The anion of IX is first generated by treating IX in a solvent with any suitable base. Examples of solvents that may be used include ethereal solvents such as THF, DME, dioxane, diethyl ether, methyl-tert-butyl ether; aromatic hydrocarbons, such as benzene, toluene, xylene; halogenated hydrocarbons, such as dichloromethane, carbon tetrachloride, dichloroethane; or other organic solvents, such as acetonitrile. Preferred solvents include THF, DME, toluene or dichloromethane. Suitable bases for generating the anion include organic bases such as an alkali metal hydride, an alkali metal tert-butoxide, an alkyl or aryl lithium, such as methyl-, butyl- or phenyllithium; an alkali metal amide, such as lithium-, sodium- or potassium bis(trimethylsilyl) amide, diisopropylamide, or tetramethylpiperidine. Preferred bases include lithium bis(trimethylsilyl)amide, lithium diisopropylamide, or lithium tetramethylpiperidine. The anion of IX is treated with the carboxylic acid equivalent at a reaction temperature that may be in the range of about –78° C. to 120° C., preferably between about 0° C. to 60° C.

The azidobutenolactone VIII may be obtained from VII by the displacement of its substituent X with an azide. For the reaction of VII where its substituent X is bromo, VII is preferably treated with an alkali or alkaline earth salt of azide, such as $NaN_3$ or $LiN_3$. A silylazide ($N_3$—Y where Y is a silyl group as described above) may be used in the presence of a fluoride reagent, such as tetrabutylammonium fluoride, cesium fluoride, potassium fluoride, sodium fluoride or the like, to generate the nucleophilic azide anion. Suitable solvents include non-protic organic solvents, such as acetone, NMP, MEK, THF, DME, and dioxane, and halogenated hydrocarbons, such as chloroform, carbon tetrachloride, dichloromethane, and dichloroethane. The reaction is run at a temperature in the range of about 0° C. to 100° C., preferably between about 20° C. to 40° C.

The reduction of the furanone ring double bond in X to provide I may be accomplished with a hydride reducing agent, especially a borohydride. Examples of such borohydrides include sodium or lithium borohydride, sodium or lithium triacetoxyborohydride, sodium or lithium cyanoborohydride, tetrabutylammonium cyanoborohydride, sodium or lithium trialkylborohydride, preferably sodium cyanoborohydride. Typically the reaction mixture is adjusted to be mildly acidic, preferably at a pH between 3.0 and 6.0 with acids such as HCl, HBr, acetic acid, formic acid, trifluoroacetic acid, $BF_3.OEt_2$, aluminum trichloride, zinc chloride, or titanium tetrachloride. Optionally, the reaction may be buffered with 1.0–5.0 equivalents of sodium acetate. Optionally, the reaction may be catalyzed by the addition of 1–5% $COCl_2$/semicorrin, $ZnCl_2$, or 1–2 equivalents of chlorotrimethylsilane. Chiral hydride reducing agents are known such as R- or S-Alpine Hydride® (lithium B-isopinocampheyl-9-bora-bicyclo[3.3.1]nonyl hydride to provide asymmetric reduction.

Reduction of the ring double bond in X to provide I may also be accomplished by hydrogenation. This is useful when $R^1$ is stable to the hydrogenation conditions, such as when $R^1$ is alkyl. Typical hydrogenation conditions include hydrogen gas at a pressure in the range of about one to 100 atmospheres, usually between about 15 to 70 atmospheres, and a catalyst present in the range of about 0.01 to 0.5 equivalents per equivalent of X. Suitable catalysts include Pd/C, Pd(OH)2, PdO, Pt/C, PtO2, preferentially Pt/C or Pd/C. Suitable solvents include ethyl acetate, alcohols, such as methanol, ethanol, isopropanol, aromatic hydrocarbons, such as benzene, toluene, xylene, ethereal such as THF, DME, dioxane, preferentially ethanol or THF. When $R^1$ is alkyl or aralkyl, such as benzyl, a rhodium (I) or ruthenium (II) catalyst is preferred for stereoselective reduction. Such catalyst is formed by reacting the metal as one of its various complexes with chiral forms of ligands such as methyl- or ethyl-DuPHOS (1,1-bis-2,5-dialkylphospholano)benzene, DIOP (2,3-O-isopropylidene-2,3-dihydroxy-1,4-bis (diphenylphosphino)butane), BINAP (2,2'-bis (diphenylphosphino)-1,1'-binaphthyl), CHIRAPHOS (bis (diphenylphosphino)butane), BPPM (N-t-butoxycarbonyl-2-(diphenylphosphino)methyl-4-(diphenylphosphino) pyrrolidine), BPPFA (N,N-dimethyl-1-[1',2-bis (diphenylphosphino)ferrocenyl]ethylamine), DEGPHOS(N-benzyl-3,4-bis(diphenylphosphino)pyrrolidine), or alkyl-BPE (bisphospholanoethane). Many other suitable ligands are known in the art. Preferred catalysts are 1,2-bis(2,5-dialkylphospholano)benzene(cyclooctadiene)rhodium(I) trifluoromethanesulfonate, where alkyl is a straight chain or branched alkyl group of 1–8 carbons, optionally substituted with an aromatic hydrocarbon such as phenyl. Use of the (R,R) isomer of these ligands will lead to the (S)-configuration of the α-amino carbon in the product and use of the (S,S) isomer will lead to the (R)-configuration. Suitable solvents include ethyl acetate, alcohols, such as methanol, ethanol, or isopropanol, aromatic hydrocarbons, such as benzene, toluene, or xylene, ethers such as THF, DME, or dioxane. Preferred solvents are toluene or methanol. The reaction concentration of X will typically be in the range of about 0.01M to 1.0M, preferably about 0.1M to 1.0M. The reaction temperature is usually in the range of about 0° C. to 60° C., preferably between about 20° C. to 40° C. (For the use of rhodium catalysts see: G. Zhu, Z. Chen, X. Zhang; *J. Org. Chem.* (1999) 64, 6907–6910; M. J. Burk, J. G. Allen, W. F. Kiesman; *J. Amer. Chem. Soc.,* (1998), 120, 657–663; M. J. Burk, J. E. Feaster, W. A. Nugent, R. L. Harlow; *J. Amer. Chem. Soc.,* (1993), 115, 10125–10138; For the use of ruthenium catalysts see: J. M. Brown, M. Rose, F. I. Knight, A. Wienand; *Recl Trav Chim Pays-Bas,* (1995), 114, 242–251; M. Saburi, M. Ohnuki, M. Ogasawara, T. Takahashi, Y. Uchida; *Tetrahedron Lett.* (1992), 33, 5783–5786; U Matteoli, V. Beghetto, A. Scrivanti; *J Molecular Catalysis A: Chemical* 140 (1999) 131–137).

Method B above describes a sequence in which the aminobutenolactone IX is first coupled to a caspase $P_x$ or $P_{x-y}$ moiety and then the ring double bond is reduced. Alternatively, the reduction and coupling may be performed in reverse order (Method C). Method C of the present process comprises the steps of:

(a) providing a butenolactone VII:

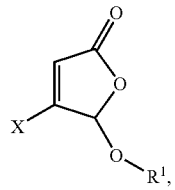

wherein $R^1$ is as described above, and X is chloro, bromo or iodo;

(b) treating VII with an azide $N_3$—Y, where Y is a silyl group or a counterion, to form an azidobutenolactone VIII:

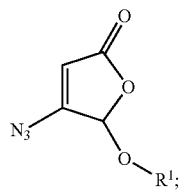

(c) converting VIII to an aminobutenolactone IX:

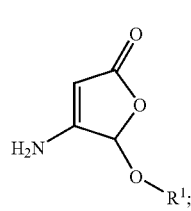

(d) reducing the ring double bond of IX to provide the aminolactone IV:

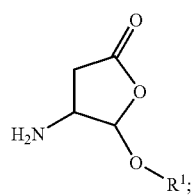

(e) coupling IV with an organic acid $R^2COOH$, or reactive equivalent thereof, to form I, where $R^2COOH$ is preferably a $P_2$—, $P_2$—$P_3$—, or $P_2$—$P_4$ carboxylic acid. In Method C, steps (a)–(c) are the same as the corresponding steps in Method B, and steps (d) and (e) are the same as the corresponding steps in Method A. Therefore, Method C may be carried out in a like manner with respect to the corresponding steps.

Within the scope of this invention are certain intermediates described herein that are useful in the preparation of the caspase inhibitors and prodrugs thereof. Therefore, one aspect of this invention relates to compounds of formula III or VIII:

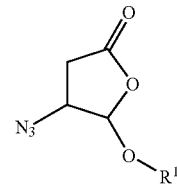

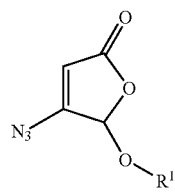

wherein $R^1$ is selected from an optionally substituted aliphatic group, aralkyl group or aryl group. Examples of $R^1$ include methyl, ethyl, propyl, 2-propyl, butyl, pentyl, hexyl, 4-methylpentyl, 2-methylpropyl, cyclopentyl, cyclohexyl, cyclopentylmethyl, cyclohexylmethyl, phenylethyl, phenylpropyl, phenylbutyl, (d)-menthyl, (l)-menthyl, 1-adamantyl, 2-adamantyl, 1-indanyl, 2-indanyl, bornyl, 3-tetrahydrofuranyl, benzyl, α-methylbenzyl, 4-chlorobenzyl, 4-fluorobenzyl, 4-methylbenzyl, 4-(2-propyl)benzyl, or 4-trifluoromethylbenzyl. Particularly useful are III and VIII where $R^1$ is benzyl or a $C_{1-6}$ alkyl such as ethyl.

Another aspect of this invention relates to compounds of formula

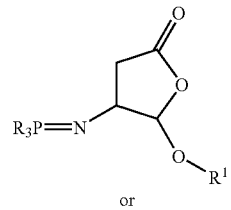

or

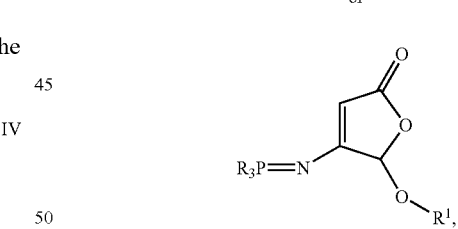

wherein $R^1$ is selected from an optionally substituted aliphatic group, aralkyl group or aryl group, and in particular, the $R^1$ groups described above.

In order that this invention be more fully understood, the following preparative examples are set forth. These examples are for the purpose of illustration only and are not to be construed as limiting the scope of the invention in any way.

SYNTHETIC EXAMPLES

Example 1

Preparation of 4-azido-5-ethoxy-dihydrofuran-2-one (III, $R^1$=Et)

This procedure was carried out in a manner similar to that described by D. J. Guerin, et al., *Org. Lett* (1999), 1, 1107–1109. To a solution of azidotrimethylsilane (25.8 mL, 0.32 mol) in dichloromethane (400 mL) at room temperature under nitrogen was added acetic acid (18.1 mL, 0.32 mol), and the reaction was stirred for 20 min. 5-Ethoxy-5H-furan-2-one (II, $R^1$=Et) (8.10 g, 0.063 mol) was added dropwise, followed by 1,8-diazabicyclo[5.4.0]undec-7-ene (1.9 mL, 0.013 mol). The reaction was stirred for 24 h, washed with sodium bicarbonate, dried over sodium sulfate and evaporated. Purification by flash chromatography ($SiO_2$) eluted with 1:9 ethyl acetate:hexanes afforded 4-azido-5-ethoxy-dihydrofuran-2-one (7.85 g, 73% yield) as a colorless oil.

$^1$H-NMR (500 MHz, $CDCl_3$) δ 5.17 (s, 1H), 4.00 (dd, J=7.0, 1.0 Hz, 1H), 3.71 (m, 1H), 3.49 (m, 1H), 2.77 (dd, J=17.0, 6.0 Hz, 1H), 2.32 (dd, J=8.0, 2.2 Hz, 1H), 1.08 (t, J=7.1 Hz, 1.5H), 1.07 (t, J=7.1 Hz, 1.5H) ppm.

In a manner similar to that described above, except starting with 5-benzyloxy-5H-furan-2-one (II, $R^1$=Bn), 4-azido-5-benzyloxy-dihydrofuran-2-one (III, $R^1$=Bn) was prepared as a white solid, 1.62 g (72% yield). $^1$H-NMR (500 MHz, $CDCl_3$) δ 7.19 (m, 5H), 5.25 (s, 1H), 4.71 (d, J=11.5 Hz, 1H), 4.48 (d, J=11.4 Hz, 1H), 4.07 (dd, J=6.9, 0.9 Hz, 1H), 2.82 (ddd, J=18.1, 7.1, 1.0 Hz, 1H), 2.36 (ddd, J=18.1, 4.3, 1.4 Hz, 1H) ppm.

Example 2

Preparation of 4-[(triphenylphosphoranylidene)-amino]-5-ethoxy-dihydrofuran -2-one (V, $R^1$=Et)

A solution of 4-azido-5-ethoxy-dihydrofuran-2-one (0.05 g, 0.29 mmol) and triphenylphosphine (0.078 g, 0.29 mmol) in toluene (5 mL) was stirred at room temperature under nitrogen for 5 h. The solvent was evaporated to afford 4-[(triphenylphosphoranylidene)amino]-5-ethoxy-dihydrofuran -2-one (0.12 g, 100% yield) as an off-white, waxy solid. $^1$H-NMR (500 MHz, $CDCl_3$) δ 7.50 (m, 6H), 7.40 (m, 3H), 7.33 (m, 6H), 5.08 (d, J=3.1 Hz, 1H), 3.63 (m, 1H), 3.23 (m, 1H), 2.50 (dd, J=17.1, 5.9 Hz, 1H), 2.27 (dd, J=17.1, 5.9 Hz, 1H), 0.91 (t, J=7.0 Hz, 3H) ppm.

Example 3

Preparation of (R)-2-(2-ethoxy-5-oxo-tetrahydrofuran -3-ylcarbamoyl)-pyrrolidine-1-carboxylic acid tert-butyl ester (I, $R^1$=Et)

Method 1. From 4-azido-5-ethoxy-dihydrofuran-2-one Via Hydrogenation:

A mixture of 4-azido-5-ethoxy-dihydrofuran-2-one (1.06 g, 6.2 mmol), (S)-pyrrolidine-1,2-dicarboxylic acid 1-tert-butyl ester (1.33 g, 6.2 mmol), and 10% palladium on carbon (0.50 g) in ethyl acetate previously degassed with $N_2$ (50 mL) was stirred under 1 atm hydrogen at room temperature for 1 h. The mixture was diluted with dichloromethane, filtered (Celite) and evaporated. The crude mixture was dissolved in dichloromethane (100 mL), was treated with diisopropylethylamine (5.4 mL, 30.8 mmol), EDC (1.48 g, 7.71 mmol), and HOBT (1.04 g, 7.71 mmol) and was stirred at room temperature under nitrogen for 24 h. The reaction was diluted with ethyl acetate, was washed with 10% sodium bisulfate, saturated sodium bicarbonate, and brine, was dried over sodium sulfate, and was evaporated. Purification by flash chromatography ($SiO_2$) eluted with 1:1 ethyl acetate:hexanes provided (R)-2-(2-ethoxy-5-oxo-tetrahydrofuran-3-ylcarbamoyl)-pyrrolidine-1-carboxylic acid tert-butyl ester (1.19 g, 56% yield) as a very viscous, pale yellow oil. $^1$H-NMR (500 MHz, $CDCl_3$) δ 7.61 (br, 0.6H), 5.29 (s, 0.6H), 5.25 (br s, 0.4H), 4.29 (br, 1.2H), 4.20 (br s, 0.8H), 3.78 (m, 1H), 3.57 (m, 1H), 3.34 (br, 1.4H), 3.25 (br, 0.6H), 2.94 (br dd, J=14.9, 3.8 Hz, 1H), 2.31 (dd, J=18.0, 1.4 Hz, 1H), 2.1–2.3 (br 1H), 1.82 (br s, 1H), 1.39 (s, 9H), 1.17 (m, 3H) ppm. MS (ES+): m/e=343 (M+H).

Method 2. From 4-[(triphenylphosphoranylidene)amino]-5-ethoxy-dihydrofuran-2-one:

A solution of (S)-pyrrolidine-1,2-dicarboxylic acid 1-tert-butyl ester (0.11 g, 0.5 mmol), di-isopropylethylamine (0.18 mL, 1.0 mmol), and tetramethylfluoroformamidinium hexafluorophosphate (TFFH) (0.13 g, 0.5 mmol) in dichloromethane (3 mL) was stirred at room temperature under nitrogen for 3 h. A solution of 4-[(triphenylphosphoranylidene)amino]-5-ethoxy-dihydrofuran -2-one (0.20 g, 0.5 mmol) in dichloromethane (3 mL) was added and the mixture was stirred for 24 h. The reaction was diluted with ethyl acetate, was washed with 10% sodium bisulfate, saturated sodium bicarbonate, and brine, was dried over sodium sulfate, and was evaporated. Purification by flash chromatography ($SiO_2$) eluted with 1:1 ethyl acetate:hexanes provided (R)-2-(2-ethoxy-5-oxo-tetrahydrofuran -3-ylcarbamoyl)-pyrrolidine-1-carboxylic acid tert-butyl ester (0.11 g, 65% yield) as a very viscous, pale yellow oil.

Method 3. From (R)-2-(2-ethoxy-5-oxo-2,5-dihydrofuran-3-ylcarbamoyl)-pyrrolidine-1-carboxylic Acid Tert-Butyl Ester (X, $R^1$=Et) Via Hydrogenation:

To a solution of (R )-2-(2-ethoxy-5-oxo-2,5-dihydrofuran-3-ylcarbamoyl)-pyrrolidine-1-carboxylic acid tert-butyl ester (X, $R^1$=Et) (0.09 g, 0.27 mmol) in toluene previously degassed with $N_2$ (20 mL) in a high pressure reactor in a nitrogen filled glove bag, was added (–)-1,2-bis((2R,5R)-2,5-diethyl-pholano)benzene-(cyclooctadiene)rhodium(I) trifluoromethanesulfonate (5–15 mg). The reactor was sealed and pressurized with hydrogen (950 psi, 65 atm) and was let stand at room temperature for 2 d. Solvent was evaporated and the residue was purified by flash chromatography ($SiO_2$) eluted with 1.5:98.5 methanol:dichloromethane to provide (R)-2-(2-ethoxy-5-oxo-tetrahydrofuran-3-ylcarbamoyl)-pyrrolidine-1-carboxylic acid tert-butyl ester (0.092 g, quant yield) as a colorless oil. Chiral HPLC (chiralpak-AD column, eluted with 1:9 ethanol:hexanes): isomer Ib-35.4%, isomer Id-56.4%, (mixture of isomers Ia and Ic)-8.2%. $^1$H-NMR (500 MHz, $CDCl_3$) δ 7.60 (br s, 0.25H), 7.40 (br s, 0.25H), 6.5 (br m, 0.25H), 5.38 (d, J=5 Hz, 0.5H), 5.27 (s, 0.5H), 4.65 (br, 0.5H), 4.20 (br m, 1.5H), 3.85 (m, 0.5H), 3.77 (m, 0.5H), 3.57 (m, 1H), 3.30 (m, 2H), 2.95 (m, 0.5H), 2.80 (br m, 0,5H), 2.30 (br m, 2H), 1.85 (br s, 3H), 1.37 (s, 9H), 1.20 (t, J=7 Hz, 1.5H), 1.15 (t, J=7 Hz, 1.5H) ppm.

Example 4

Preparation of (R)-2-(2-benzyloxy-5-oxo-tetrahydrofuran -3-ylcarbamoyl)-pyrrolidine-1-carboxylic acid tert-butyl ester (I, $R^1$=Bn)

A solution of (S)-pyrrolidine-1,2-dicarboxylic acid 1-tert-butyl ester (0.13 g, 0.6 mmol), 4-azido-5-benzyloxy-dihydrofuran-2-one (0.14 g, 0.6 mmol) and triphenylphosphine (0.28 g, 1.0 mmol) in tetrahydrofuran (5 mL) and water (5 drops) was stirred under nitrogen for 0.5 h at room temperature and for 2 h at 65° C. The reaction was cooled to room temperature, was treated with with di-isopropylethylamine (0.52 mL, 5.0 mmol), EDC (0.15 g, 0.75 mmol), and HOBT (0.10 g, 0.75 mmol) and was stirred at room temperature under nitrogen for 20 h. The reaction was diluted with ethyl acetate, was washed with 10% sodium bisulfate, saturated sodium bicarbonate, and brine, was dried over sodium sulfate, and was evaporated. Purification by flash chromatography (SiO$_2$) eluted with 2:3 ethyl acetate:hexanes provided (R)-2-(2-benzyloxy-5-oxo-tetrahydrofuran-3-ylcarbamoyl)-pyrrolidine-1-carboxylic acid tert-butyl ester (0.12 g, 49% yield) as a sticky resin. $^1$H-NMR (500 MHz, CDCl$_3$) δ 7.63 (br d, J=7.6 Hz, 0.7H), 7.28 (m, 5H), 6.50 (br, 0.3H), 5.37 (br s, 0.5H), 5.33 (s, 0.5H), 4.77 (d, J=11.6 Hz, 1H), 4.56 (dd, J=11.6, 3.7 Hz, 1H), 4.37 (br s, 1H), 4.18 (br s, 1H), 3.32 (br s, 1.4H), 3.24 (br s, 0.6H), 2.97 (br d, J=11.6 Hz, 1H), 2.35 (dd, J=18.1, 1.7 Hz, 1H), 2.1–2.3 (br, 1H), 1.81 (br s, 3H), 1.58 (s, 9H) ppm. MS (ES+): m/e=405 (M+H).

In a similar manner, (R)-2-(2-ethoxy-5-oxo-tetrahydrofuran -3-ylcarbamoyl)-pyrrolidine-1-carboxylic acid tert-butyl ester (I, R=Et) (0.07 g, 7% yield) was prepared.

Example 5

Preparation of 4-bromo-5-ethoxy-5H-furan-2-one (VII, R$^1$=Et)

This procedure was carried out in a manner similar to that described by C. Escobar, et al., *Ann. Quim.* (1971), 67, 43–57.). To a solution of 5-ethoxy-5H-furan-2-one (II, R$^1$=Et) (10.0 g, 78.0 mmol) in carbon tetrachloride (50 mL) at 0° C. was added over 0.5 h a solution of bromine (4.05 mL, 78.2 mmol) in carbon tetrachloride (25 mL). The reaction was stirred 1 h at 0° C., then 2 h at room temperature. The solvents were removed under reduced pressure and the residue was short-path distilled at pump vacuum (about 0.5 mm). The fraction collected at 100° C.–120° C. provided 4-bromo-5-ethoxy-5H-furan-2-one (13.2 g, 82% yield) as a yellow oil. $^1$H-NMR (500 MHz, CDCl$_3$) δ 6.24 (s, 1H), 5.63 (s, 1H), 3.71 (m, 1H), 3.63 (m, 1H), 1.14 (t, J=7.1 Hz, 3H) ppm.

Example 6

Preparation of 4-azido-5-ethoxy-5H-furan-2-one (VIII, R$^1$=Et)

A mixture of 4-bromo-5-ethoxy-5H-furan-2-one (2.07 g, 10.0 mmol) and sodium azide (0.66 g, 10.2 mmol) in dimethylformamide (10 mL) was stirred at room temperature under nitrogen for 24 h. The reaction was diluted with ethyl acetate, was washed with 0° C. water and with brine, was dried over sodium sulfate, and was evaporated. Purification by flash chromatography (SiO$_2$) eluted with 1:9 ethyl acetate:hexanes afforded 4-azido-5-ethoxy-5H-furan-2-one (1.04 g, 62% yield) as a pale yellow oil. $^1$H-NMR (500 MHz, CDCl$_3$) δ 5.83 (s, 1H), 5.63 (s, 1H), 3.99 (m, 1H), 3.88 (m, 1H), 1.35 (t, J=7.1 Hz, 3H) ppm.

Example 7

Preparation of 4-amino-5-ethoxy-5H-furan-2-one (IX, R$^1$=Et)
Method 1. Via Hydrogenation:
A mixture of 4-azido-5-ethoxy-5H-furan-2-one (0.62 g, 3.67 mmol) and 10% palladium on charcoal (0.31 g) in de-oxygenated ethyl acetate (20 mL) was stirred at 1 atm hydrogen for 24 h. The reaction was filtered (Celite) and evaporated to provide 4-amino-5-ethoxy-5H-furan -2-one (0.53 g, 100% yield) as a yellow oil. $^1$H-NMR (500 MHz, CDCl$_3$) δ 5.60 (s, 1H), 4.85 (br s, 2H), 4.81 (s, 1H), 3.81 (m, 1H), 3.67 (m, 1H), 1.22 (t, J=7.1 Hz, 3H) ppm.
Method 2. Via Staudinger Reacion:
A mixture of 4-azido-5-ethoxy-5H-furan-2-one (0.10 g, 0.59 mmol) and triphenylphosphine (0.15 g, 0.59 mmol) in tetrahydrofuran (5 mL) and water (0.5 mL) was stirred for 20 h at room temperature, followed by 3d at 65° C. under nitrogen. The reaction was diluted with dichloromethane, washed with water, dried over sodium sulfate and evaporated to afford 4-amino-5-ethoxy-5H-furan-2-one in a mixture with triphenylphosphine oxide (0.25 g, 100% yield).

Example 8

Preparation of 4-[(triphenylphosphoranylidene) amino]-5-ethoxy-5H-furan-2-one (X$^1$, R$^1$=Et)

A solution of 4-azido-5-ethoxy-5H-furan-2-one (0.17 g, 1.0 mmol) and triphenylphosphine (0.26 g, 1.0 mmol) in toluene (5 mL) at room temperature under nitrogen was stirred for 1 h, then heated at 60–70° C. for 8 h. The reaction was cooled, was diluted with ethyl acetate, was washed with sodium bisulfate, sodium bicarbonate and brine, was dried over sodium sulfate and was evaporated. Purification by flash chromatography (SiO$_2$) eluted with 1:1 ethyl acetate:hexanes afforded 4-[(triphenylphosphoranylidene)amino]-5-ethoxy-5H-furan-2-one (0.18 g, 45% yield) as an off-white solid. $^1$H-NMR (500 MHz, CDCl$_3$) δ 7.73 (m, 6H), 7.65 (m, 3H), 7.55• (m, 6H), 5.58 (s, 1H), 4.33 (s, 1H), 3.81 (m, 1H), 3.64 (s, 1H), 1.27 (t, J=7.1 Hz, 3H) ppm. MS (ES+) m/e=404 (M+H).

Example 9

Preparation of (R )-2-(2-ethoxy-5-oxo-2,5-dihydrofuran-3-ylcarbamoyl)-pyrrolidine-1-carboxylic acid tert-butyl ester (X, R$^1$=Et)
Method 1. Via Peptide Coupling Conditions:
A solution of 4-amino-5-ethoxy-5H-furan-2-one (0.04 g, 0.30 mmol), (S)-pyrrolidine-1,2-dicarboxylic acid 1-tert-butyl ester (0.07 g, 0.30 mmol), diisopropylethylamine (0.12 mL, 0.66 mmol) and O-benzotriazol-1-yl-N,N,N',N'-tetramethyluronium hexafluorophosphate (HBTU) (0.14 g, 0.38 mmol) in dichloromethane (3 mL) was stirred 24 h, was evaporated, was redissolved in 1-methyl-pyrrolidinone (3 mL) and was stirred 3 d. The reaction was diluted with ethyl acetate, was washed with 10% sodium bisulfate, saturated sodium bicarbonate, and brine, was dried over sodium sulfate, and was evaporated. Purification by two flash chromatographies (SiO$_2$), eluted first with 4:6, then with 35:65 ethyl acetate:hexanes afforded (R )-2-(2-ethoxy-5-oxo-2,5-dihydrofuran-3-ylcarbamoyl)-pyrrolidine-1-carboxylic acid tert-butyl ester (0.009 g, 9% yield) as a film. $^1$H-NMR (500 MHz, CDCl$_3$) δ 10.2 (br s, 0.7H), 10.1 (br s, 0.3H), 6.21 (br s, 0.7H), 6.17 (br s, 0.3H), 5.68 (s, 0.7H), 5.60 (br s, 0.3H), 4.38 (br s, 1H), 3.85 (m, 1H), 3.72 (m, 1H), 3.25–3.45 (m, 2H), 2.53 (br d, 12.5 Hz, 0.7H), 2.1 (br, 0.3H), 1.87 (br m, 3H), 1.44 (s, 9H), 1.21 (m, 3H) ppm. MS (ES+): m/e=341 (M+H).
Method 2(A). Via Anion Formation/Acylation:
To a solution of 4-amino-5-ethoxy-5H-furan-2-one (0.08 g, 0.58 mmol) in tetrahydrofuran (10 mL) at −78° C. under nitrogen was dropwise added a solution of 1M lithium bis(trimethylsilyl)amide in tetrahydrofuran (0.64 mL, 0.64 mmol). The reaction was stirred 3 h at 0° C. A solution of 2-fluorocarbonyl-pyrrolidine-1-carboxylic acid tert-butyl ester (0.20 g, 0.77 mmol) in tetrahydrofuran (3 mL) was added dropwise. The reaction was stirred for 16 h at room temperature. The mixture was diluted with ethyl acetate, was washed with 10% sodium bisulfate, saturated sodium bicarbonate, and brine, was dried over sodium sulfate, and was evaporated. Purification by flash chromatography (SiO$_2$) eluted with 35:65 ethyl acetate:hexanes afforded (R )-2-(2-ethoxy-5-oxo-2,5-dihydrofuran-3-ylcarbamoyl)-pyrrolidine-1-carboxylic acid tert-butyl ester (0.05 g, 26% yield). Also isolated was starting 4-amino-5-ethoxy-5H-furan-2-one (0.03 g, 36% yield).

Method 2(B). Via Anion Formation/Acylation:

To a solution of 4-amino-5-ethoxy-5H-furan-2-one (0.05 g, 0.35 mmol) and 2-fluorocarbonyl-pyrrolidine-1-carboxylic acid tert-butyl ester (0.09 g, 0.42 mmol) in tetrahydrofuran (5 mL) at room temperature under nitrogen was added sodium tert-butoxide(0.05 g, 0.49 mmol). The reaction was stirred 3 h at reflux. After cooling, the mixture was diluted with ethyl acetate, was washed with 10% potassium bisulfate, saturated sodium bicarbonate, and brine, was dried over sodium sulfate, and was evaporated. Purification by flash chromatography (SiO$_2$) eluted with 4:6 ethyl acetate:hexanes afforded (R)-2-(2-ethoxy-5-oxo-2,5-dihydrofuran-3-ylcarbamoyl)-pyrrolidine-1-carboxylic acid tert-butyl ester (0.075 g, 63% yield). Also recovered was starting 4-amino-5-ethoxy-5H-furan-2-one (0.016 g, 32% yield).

Example 10

Preparation of (R)-2-[(2R, 3S)-2-ethoxy-5-oxo-tetrahydrofuran-3-ylcarbamoyl]-pyrrolidine-1-carboxylic acid tert-butyl ester (VI, R$^1$=Et)

A mixture of 4-amino-5-ethoxy-5H-furan-2-one (0.13 g, 0.75 mmol), (S)-pyrrolidine-1,2-dicarboxylic acid-1-tert-butyl ester (0.16 g, 0.75 mmol) and several crystals of Congo Red indicator in ethanol (5 mL) was treated with sodium cyanoborohydride (0.06 g, 0.90 mmol), followed by dropwise addition of 4M HCl in dioxane to attain and maintain a blueish color (~pH3). The reaction was stirred 2 h, was filtered (Celite) and was evaporated. The residue was dissolved in dichloromethane (5 mL), was treated with di-isopropylethylamine (0.52 mL, 3.0 mmol), EDC (0.18 g, 0.94 mmol), and HOBT (0.13 g, 0.94 mmol) and was stirred at room temperature under nitrogen for 20 h. The reaction was diluted with ethyl acetate, was washed with 10% sodium bisulfate, saturated sodium bicarbonate, and brine, was dried over sodium sulfate, and was evaporated. Purification by flash chromatography (SiO$_2$) eluted with 1:1 ethyl acetate:hexanes provided a 4:1 mixture (by $^1$H-NMR) of (R)-2-[(2R,3S)-2-ethoxy-5-oxo-tetrahydrofuran-3-ylcarbamoyl]-pyrrolidine-1-carboxylic acid tert-butyl ester and (R)-2-[(2S,3S)-2-ethoxy-5-oxo-tetrahydrofuran-3-ylcarbamoyl]-pyrrolidine-1-carboxylic acid tert-butyl ester (0.06 g, 23% yield) as a colorless oil. $^1$H-NMR (500 MHz, CDCl$_3$) δ 7.60 (br, 0.15H), 7.44 (br s, 0.5H), 6.51 (0.35H), 5.38 (d, J=5.3 Hz, 0.8H), 5.29 (s, 0.2H), 4.65 (br m, 0.8H), 4.1–4.3 (br m, 1.2H), 3.84 (m, 0.8H), 3.78 (m, 0.2H), 3.59 (m, 1H), 3.25–3.45 (br m, 2H), 2.95 (dd, J=17.6, 7.1 Hz, 0.2H), 2.78 (br m, 0.8H), 2.34 (dd, J=17.2, 10.4 Hz, 0.8H), 1.9–2.3 (br 1.7H), 1.83 (br s, 2.5H), 1.39 (s, 9H), 1.19 (m, 3H) ppm.

Also isolated was this product, (R)-2-(2-ethoxy-5-oxo-tetrahydrofuran-3-ylcarbamoyl)-pyrrolidine -1-carboxylic acid tert-butyl ester, as a mixture of stereoisomers (0.030 g, 11% yield) as a colorless oil.

Example 11

Preparation of 1-[2-(4-amino-3-chlorobenzoylamino)-3,3-dimethylbutyryl] pyrrolidine-2-carboxylic acid (2-ethoxy-5-oxo-tetrahydrofuran-3-yl)amide Step A. {1-[2-(2-Ethoxy-5-oxo-tetrahydro-furan-3-ylcarbamoyl)-pyrrolidine-1-carbonyl]-2,2-dimethylpropyl}-carbamic Acid Benzyl Ester To a solution of (R)-2-(2-ethoxy-5-oxo-2,5-dihydrofuran-3-ylcarbamoyl)-pyrrolidine-1-carboxylic acid tert-butyl ester (X, R$^1$=Et) (0.14 g, 0.41 mmol) ($^1$H-NMR shows ~8:2 syn:anti epimers) and lutidine (0.48 mL, 4.1 mmol) in dichloromethane (5 mL) at room temperature under nitrogen was dropwise added trimethylsilyltrifluoromethane-sulfonate (0.48 mL, 2.46 mmol). The reaction was stirred for 0.5 h, then was treated with saturated sodium bicarbonate, was extracted with three portions of dichloromethane, was dried (sodium sulfate), and was evaporated. To the crude intermediate was added 2-benzyloxycarbonylamino-3,3-dimethylbutyric acid (0.12 g, 0.45 mmol) in dichloromethane (5 mL), EDC (0.10 g, 0.51 mmol) and HOBT (0.07 g, 0.51 mmol). The resulting mixture was stirred at room temperature under nitrogen for 3 days. The reaction was diluted with ethyl acetate, was washed with 10% potassium bisulfate, saturated sodium bicarbonate and brine, was dried (sodium sulfate) and was evaporated. Purification by flash chromatography (SiO$_2$) eluted with 1:1 ethyl acetate hexanes provided {1-[2-(2-ethoxy-5-oxo-tetrahydrofuran-3-yl carbamoyl)-pyrrolidine-1-carbonyl]-2,2-dimethylpropyl}carbamic acid benzyl ester (0.12 g, 59% yield) as a white foam. $^1$H-NMR (500 MHz, CDCl$_3$) δ 7.43 (br d, J=7.7 Hz, 1H), 7.28 (s, 5H), 5.40 (m, 2H), 5.02 (AB q, J=12.1, 31.0 Hz, 2H), 4.55 (m, 2H), 4.29 (d, J=9.6 Hz, 1H), 4.23 (m, 0.2H), 3.85 (m, 0.8H), 3.73 (m, 1H), 3.58 (m, 2H), 2.90 (m, 0.2H), 2.74 (dd, J=17.0, 8.4 Hz, 0.8H), 2.30 (m, 2H), 2.05 (m, 1H), 1.90 (m, 1H), 1.80 (m, 1H), 1.20 (t, J=7.0 Hz, 2.4H), 1.15 (t, J=7.0 Hz, 0.6H), 0.93 (s, 9H) ppm.

$^1$H-NMR shows ~8:2 syn:anti epimers. LC/MS (ES+): m/e=490.14 (M+H)

Step B. 1-[2-(4-amino-3-chlorobenzoylamino)-3,3-dimethylbutyryl]pyrrolidine-2-carboxylic Acid (2-ethoxy-5-oxo-tetrahydrofuran-3-yl)amide A solution of {1-[2-(2-ethoxy-5-oxo-tetrahydrofuran-3-yl carbamoyl)-pyrrolidine-1-carbonyl]-2,2-dimethylpropyl}carbamic acid benzyl ester (0.12 g, 0.24 mmol) in ethanol (5 mL) was treated with 10% palladium hydroxide on carbon (0.05 g), was stirred under 1 atm hydrogen pressure for 4 h, was filtered through Celite and was evaporated. The crude intermediate was dissolved in dichloromethane (5 mL), and was treated with 4-amino-3-chlorobenzoic acid (0.04 g, 0.26 mmol), EDC (0.06 g, 0.29 mmol) and diisopropylethylamine (0.13 mL, 0.71 mmol) and was stirred at room temperature under nitrogen for 20 h. The reaction was diluted with ethyl acetate, was washed with 10% potassium bisulfate, saturated sodium bicarbonate and brine, was dried (sodium sulfate) and was evaporated. Purification by flash chromatography (SiO$_2$) eluted with 7:3 ethyl acetate hexanes provided 1-[2-(4-amino-3-chlorobenzoylamino)-3,3-dimethylbutyryl]pyrrolidine-2-carboxylic acid (2-ethoxy-5-oxo-tetrahydrofuran-3-yl) amide (0.08 g, 62% yield) as a colorless film. $^1$H-NMR (500 MHz, CDCl$_3$) d 7.67 (d, J=2.0 Hz, 1H), 7.50 (m, 0.2H), 7.44 (dd, J=8.4, 2.0 Hz, 1.0H), 7.33 (d, J=8.0 Hz, 0.8H), 6.69 (d, J=8.4 Hz, 1H), 6.55 (d, J=9.2 Hz, 1H), 5.39 (d, J=5.2 Hz, 0.8H), 5.29 (s, 0.2H), 4.79 (d, J=9.4 Hz, 1H), 4.62 (m, 0.8H), 4.50 (m, 1.0H), 4.25 (m, 0.2H), 3.83 (m, 0.8H), 3.77 (m, 0.2H), 3.62 (m, 0.8H), 3.55 (m, 0.2H), 2.92 (m, 0.2H), 2.76

(dd, J=17.2, 8.4 Hz, 0.8H), 2.30 (m, 2H), 2.05 (m, 1H), 1.93 (m, 1.0H), 1.85 (m, 1H), 1.22 (t, J=7.1 Hz, 2.4H), 1.16 (t, J=7.1 Hz, 0.6H), 1.00 (s, 9H) ppm. $^1$H-NMR shows ~8:2 syn:anti epimers. LC/MS (ES+): m/e=509.08 (M+H).

While we have described a number of embodiments of this invention, it is apparent that our basic examples may be altered to provide other embodiments which utilize the compounds and methods of this invention. Therefore, it will be appreciated that the scope of this invention is to be defined by the appended claims rather than by the specific embodiments which have been represented by way of example.

We claim:

1. A process for making a compound of formula I:

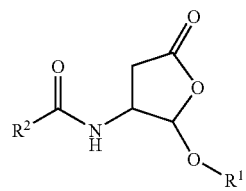

I wherein $R^1$ is an optionally substituted group selected from an aliphatic group, aralkyl group, heterocyclylalkyl group or aryl group, and $R^2$ is an organic radical, said process comprising the steps of:

(a) providing a butenolactone of formula II:

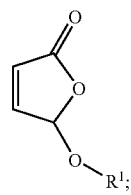

II (b) treating II with an azide $N_3$—Y, where Y is hydrogen, a silyl group, or a counterion, to form an azidolactone III:

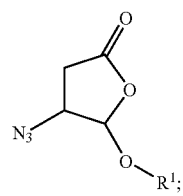

III (c) converting III to an aminolactone IV or an iminophosphorane V:

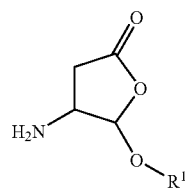

IV or

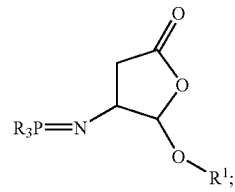

V where each R is a radical of a phosphine or a phosphinite reducing agent; and (d) coupling either IV or V with $R^2$COOH, or a reactive equivalent thereof, to form I.

2. The process of claim 1 wherein $R^2$ is a $P_4$—$P_3$—$P_2$ moiety of a caspase inhibitor, or portion thereof.

3. The process of claim 2 wherein $R^2$ is a $P_4$—$P_3$—$P_2$ moiety of a caspase inhibitor, and wherein said moiety is one of the groups:

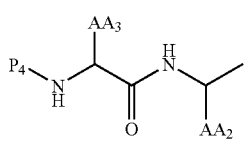

a

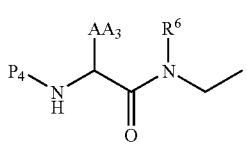

b

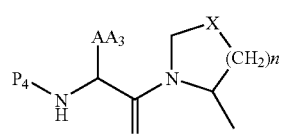

c

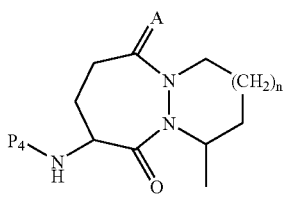

d

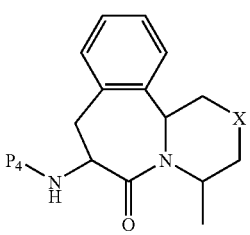

e

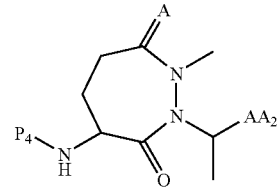

f

-continued g 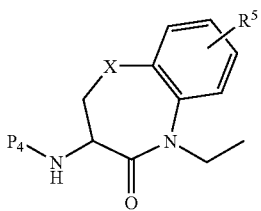

h 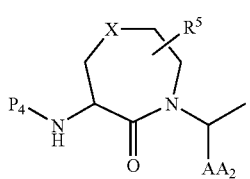

i 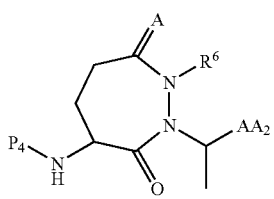

j 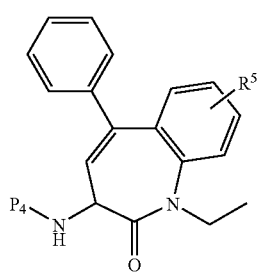

k 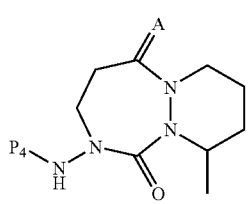

l 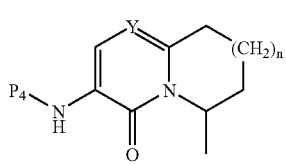

m 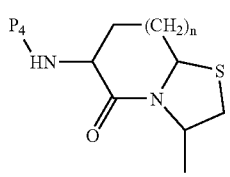

-continued n 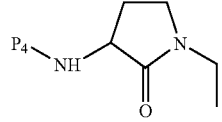

o 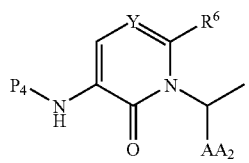

p 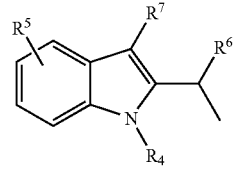

q 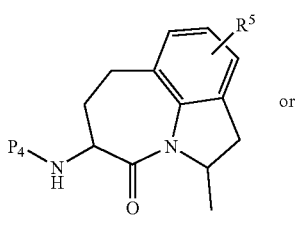

or r 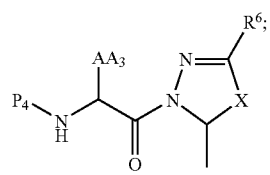

wherein:
P$_4$ is a P$_4$ moiety of a caspase inhibitor;
n is zero to three;
each AA$_2$ and AA$_3$ is independently an amino acid side chain;
X is N, O, S, SO, SO$_2$, CHF, CF$_2$, C(R$^3$)$_2$, C=O, or C=NOR';
A is O, S, or H$_2$;
Y is N or CH;
R' is hydrogen, C$_{1-12}$ alkyl group, aryl group, or heteroaryl group, the R' groups being optionally substituted with one or more halogen;
R$^3$ is an alkyl having one to six carbons;
R$^4$ is H, R$^{44}$, COR$^{44}$, S(O)$_2$R$^{44}$, or CO$_2$R$^{44}$, wherein R$^{44}$ an aliphatic group or a substituted aliphatic group;
R$^5$ is hydrogen, halo, alkyl, alkoxy, haloalkyl, haloalkoxy, amino, phenyl, phenoxy, hydroxy, alkoxycarbonyl, carboxyl, alkylcarbonyl, alkylsulfonyl, alkylsulfoxyl, alkylcarbonylamino, alkylcarbonylalkylamino, alkylamino, dialkylamino, aminosulfonyl, or cyano; and
R$^6$ and R$^7$ are independently R$^3$, aryl, heteroaryl, (C$_{1-12}$ alkyl)aryl, (C$_{1-12}$)benzocycloalkyl, or (C$_{1-12}$ alkyl)heteroaryl.

4. The process of claim 3 wherein $R^2$ is a $P_4$—$P_3$—$P_2$ moiety of a caspase inhibitor, and wherein said moiety is:
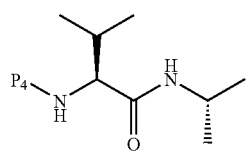
a-1
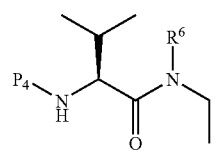
b-1
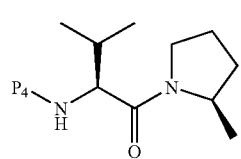
c-1
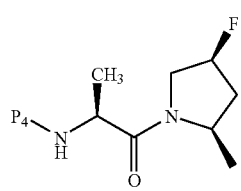
c-2
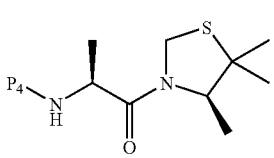
c-3
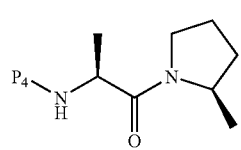
c-4
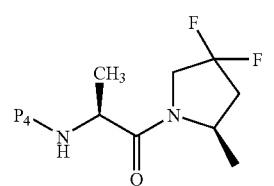
c-5
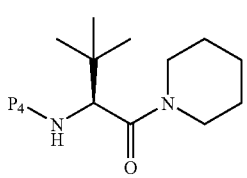
c-6
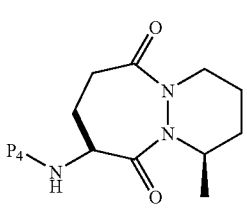
d-1
-continued
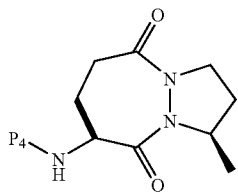
d-2
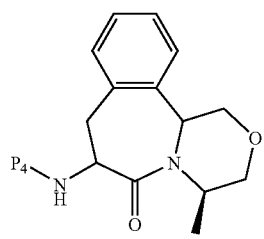
e-1
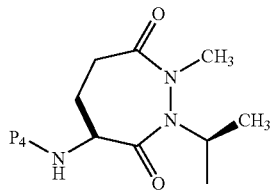
f-1
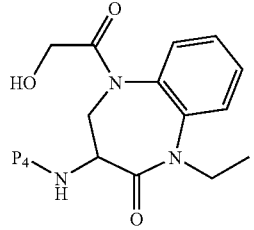
g-1
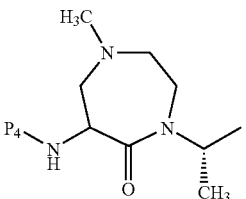
h-1
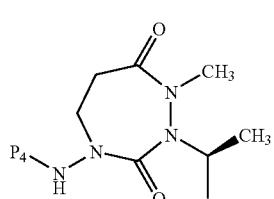
i-1
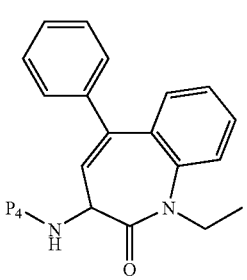
j-1 wherein:

R[6] is an optionally substituted benzyl or 2-indanyl; and

P₄ is R—T—, wherein R—T is R—CO, ROC=O, RNHC=O, RC(O)C=O, or RSO₂ and R is an optionally substituted aliphatic, aryl, or aralkyl group.

5. The process of claim 4 wherein R² is a P₄—P₃—P₂ moiety wherein the P₄ portion thereof is R—CO, ROC=O, RNHC=O, RC(O)C=O or RSO₂ and R is:

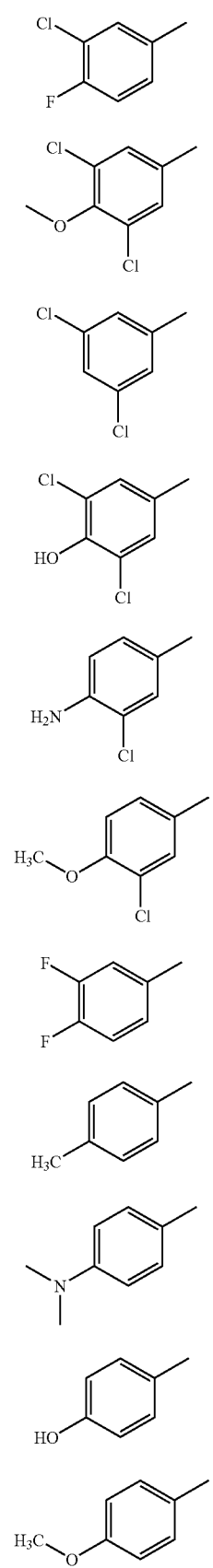
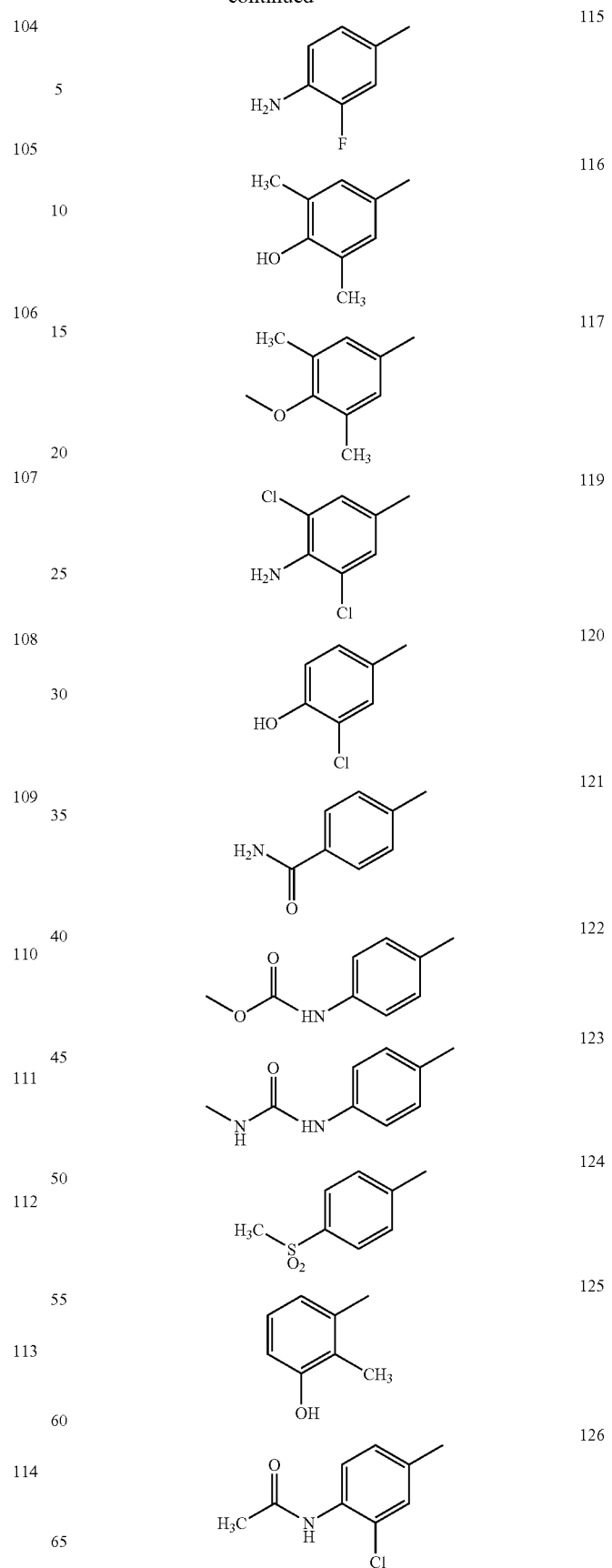

-continued
127 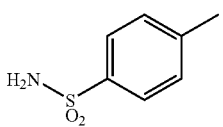
128 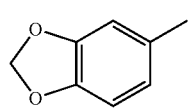
129 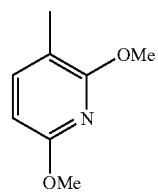
130 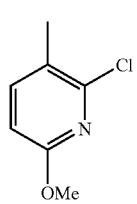
131 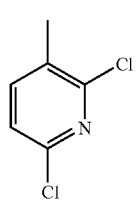
132 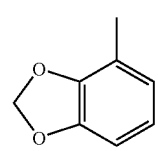
133 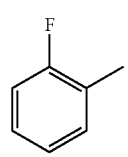
134 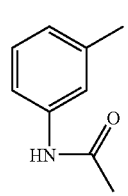
135 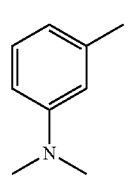
-continued
136 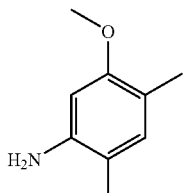
137 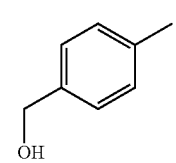
138 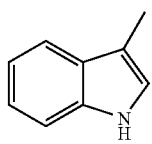
139 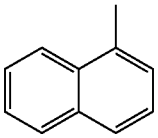
140 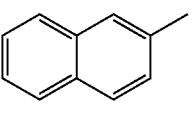
141 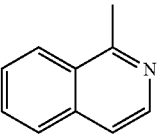
142 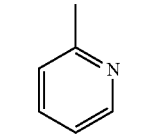
143 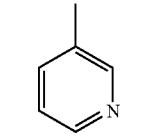
144 $C_{1–12}$ Alkyl
145 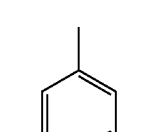
146 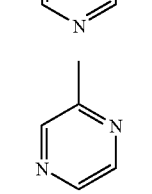

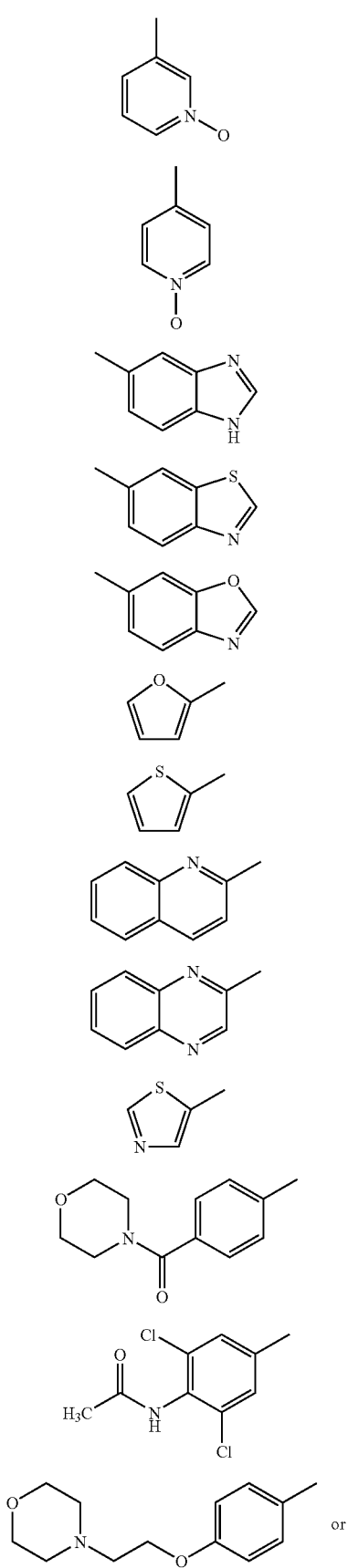
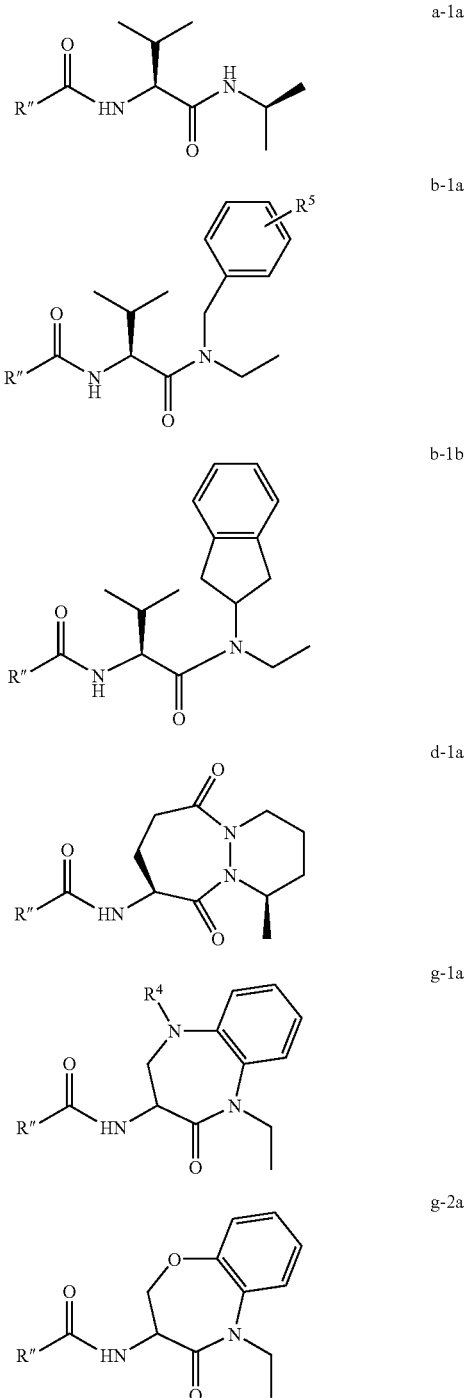
6. The process of claim 5 wherein $R^2$ is a $P_4$—$P_3$—$P_2$ moiety selected from one of the groups:

-continued

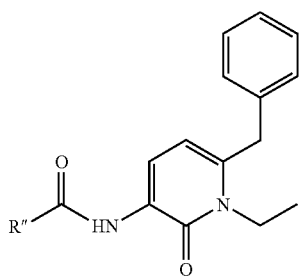
o-2a

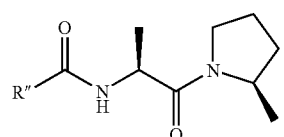
c-7a

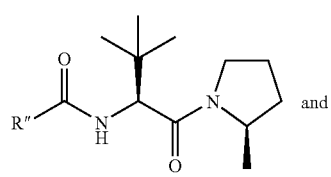
c-1a

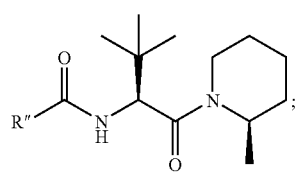
and c-6a wherein R" is:

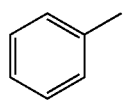
100

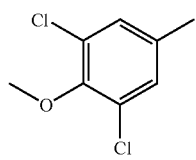
107

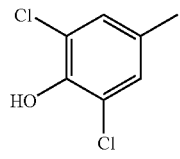
108

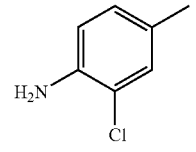
114

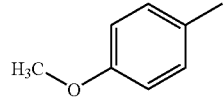

-continued

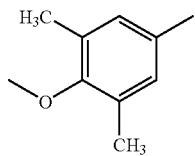
117

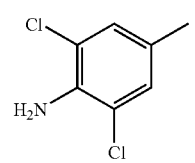
119

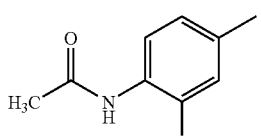
126

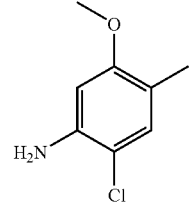
136

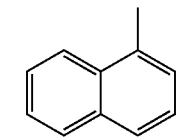
139

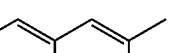
140
and

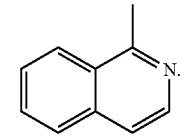
141

7. The process of claim 2 wherein $R^1$ is methyl, ethyl, propyl, 2-propyl, butyl, pentyl, hexyl, 4-methylpentyl, 2-methylpropyl, cyclopentyl, cyclohexyl, cyclopentylmethyl, cyclohexylmethyl, phenylethyl, phenylpropyl, phenylbutyl, (d)-menthyl, (l)-menthyl, 1-adamantyl, 2-adamantyl, 1-indanyl, 2-indanyl, bornyl, 3-tetrahydrofuranyl, benzyl, α-methylbenzyl, 4-chlorobenzyl, 4-fluorobenzyl, 4-methylbenzyl, 4-(2-propyl)benzyl, or 4-trifluoromethylbenzyl.

8. The process of claim 2 wherein $R^1$ is ethyl or an optionally substituted benzyl.

9. The process of claim 8 wherein $R^1$ is ethyl or benzyl.

10. The process of claim 1 or 2 wherein $N_3$—Y is selected from $LiN_3$, $NaN_3$, $TMS-N_3$, $HN_3$, or $EtAlN_3$.

11. The process of claim 1 or 2 which proceeds through the aminolactone IV.

12. The process of claim 1 or 2 which proceeds through the iminophosphorane V.

13. A process for making a compound of formula I:

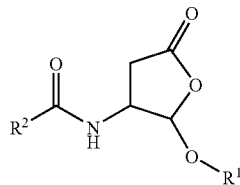

I wherein R¹ is an optionally substituted group selected from an aliphatic group, aralkyl group, heterocyclylalkyl group or aryl group, and R² is an organic radical, said process comprising the steps of:

(a) providing a butenolactone VII:

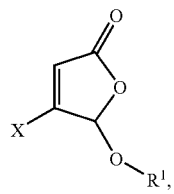

VII where X is chloro, bromo or iodo;

(b) treating VII with an azide N₃—Y, where Y is a silyl group or a counterion, to form the azidobutenolactone VIII:

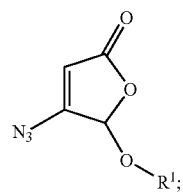

VIII (c) converting VIII to an aminobutenolactone IX or an iminophosphorane XI:

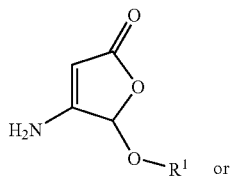

IX or

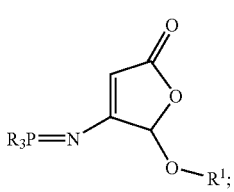

XI (d) coupling either IX or XI with R²COOH, or a reactive equivalent thereof, to form X:

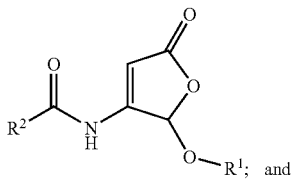

X and and where each R is a radical of a phosphine or a phosphinite reducing agent; and (e) reducing the furanone ring double bond in x to provide I.

14. The process of claim 13 wherein R² is a P₄—P₃—P₂ moiety of a caspase inhibitor, or portion thereof.

15. The process of claim 14 wherein R² is a P₄—P₃—P₂ moiety of a caspase inhibitor, wherein said moiety is:

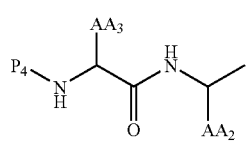

a

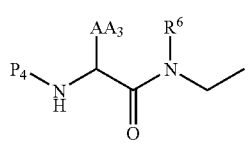

b

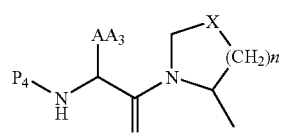

c

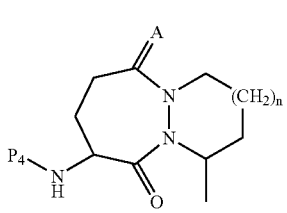

d

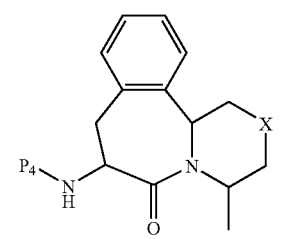

e

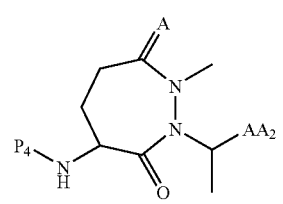

f

-continued g 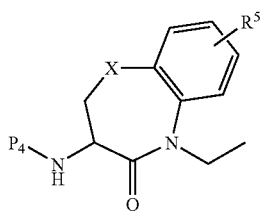

h 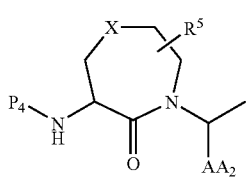

i 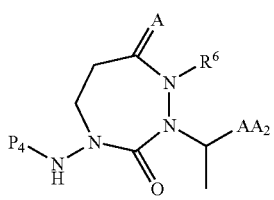

j 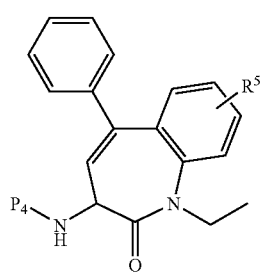

k 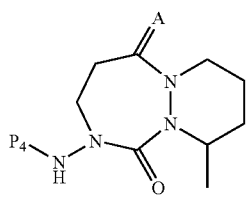

l 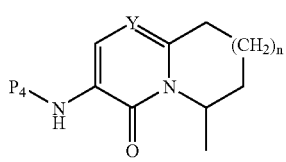

m 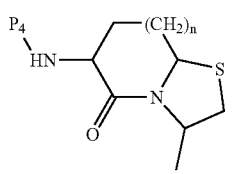

n 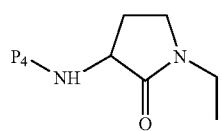

-continued o 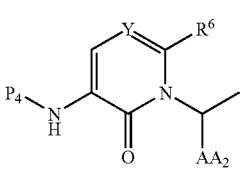

p 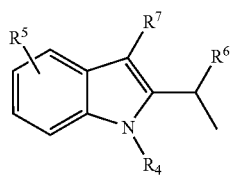

q 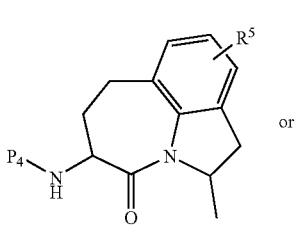

or r 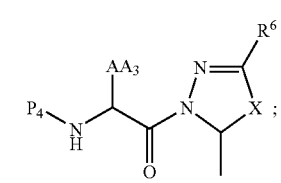

wherein:

$P_4$ is a $P_4$ moiety of a caspase inhibitor;

n is zero to three;

each $AA_2$ and $AA_3$ is an amino acid side chain;

X is N, O, S, SO, $SO_2$, CHF, $CF_2$, $C(R^3)_2$, C=O, or C=NOR';

$A_2$ is O, S, or $H_2$;

Y is N or CH;

R' is hydrogen, $C_{1-12}$ alkyl group, aryl group, or heteroaryl group, the R' groups being optionally substituted with one or more halogen;

$R^3$ is an alkyl having one to six carbons;

$R^4$ is H, $R^{44}$, $COR^{44}$, $S(O)_2R^{44}$, or $CO_2R^{44}$, wherein $R^{44}$ an aliphatic group or a substituted aliphatic group;

$R^5$ is hydrogen, halo, alkyl, alkoxy, haloalkyl, haloalkoxy, amino, phenyl, phenoxy, hydroxy, alkoxycarbonyl, carboxyl, alkylcarbonyl, alkylsulfonyl, alkylsulfoxyl, alkylcarbonylamino, alkylcarbonylalkylamino, alkylamino, dialkylamino, aminosulfonyl, or cyano; and $R^6$ and $R^7$ are independently $R^3$, aryl, heteroaryl, ($C_{1-12}$ alkyl)aryl, ($C_{1-12}$)benzocycloalkyl, or ($C_{1-12}$ alkyl) heteroaryl.

16. The process of claim 15 wherein $R^2$ is a $P_4$—$P_3$—$P_2$ moiety of a caspase inhibitor, wherein said moiety is one of the groups 2:
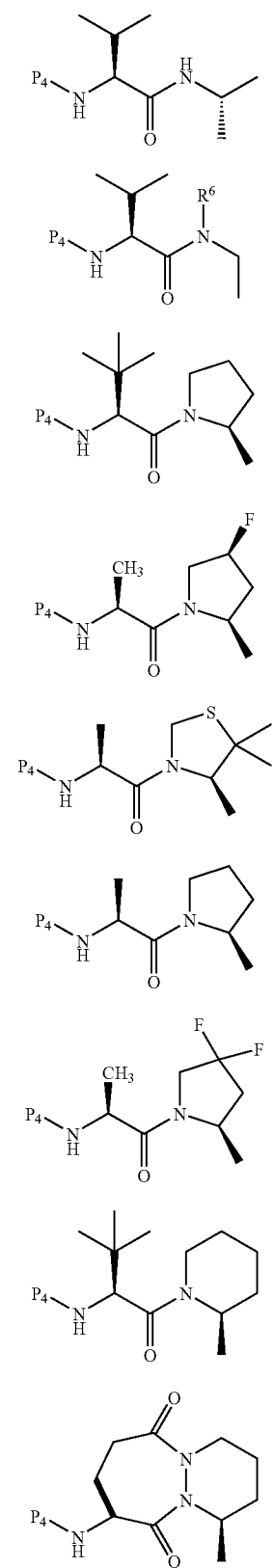
-continued
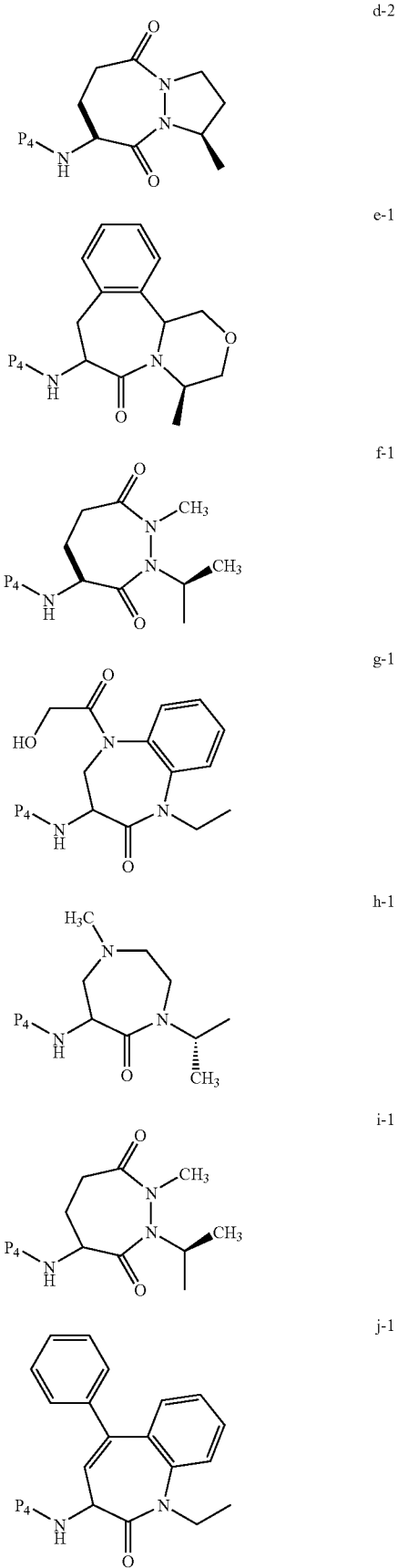

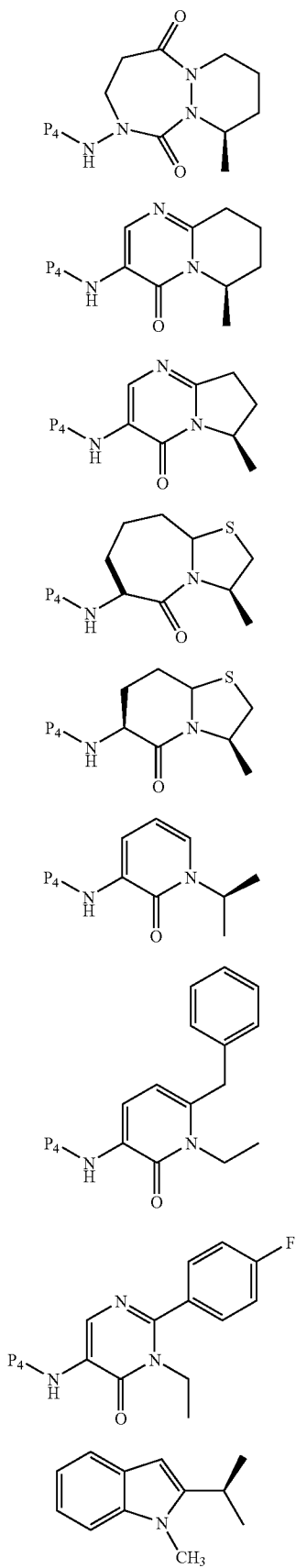
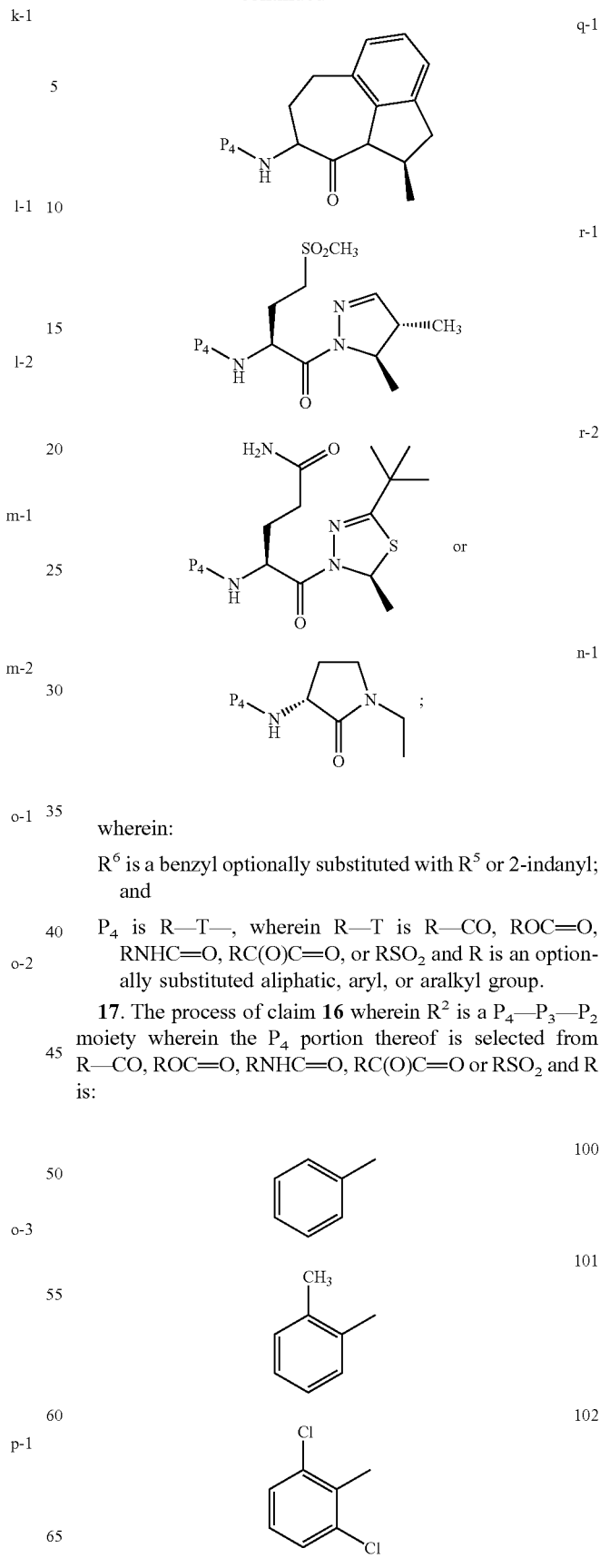
wherein:
R[6] is a benzyl optionally substituted with R[5] or 2-indanyl; and
$P_4$ is R—T—, wherein R—T is R—CO, ROC=O, RNHC=O, RC(O)C=O, or RSO$_2$ and R is an optionally substituted aliphatic, aryl, or aralkyl group.
17. The process of claim 16 wherein R[2] is a $P_4$—$P_3$—$P_2$ moiety wherein the $P_4$ portion thereof is selected from R—CO, ROC=O, RNHC=O, RC(O)C=O or RSO$_2$ and R is:

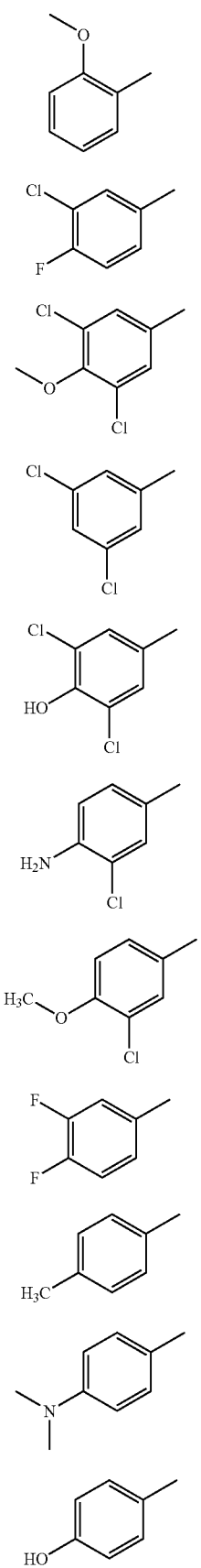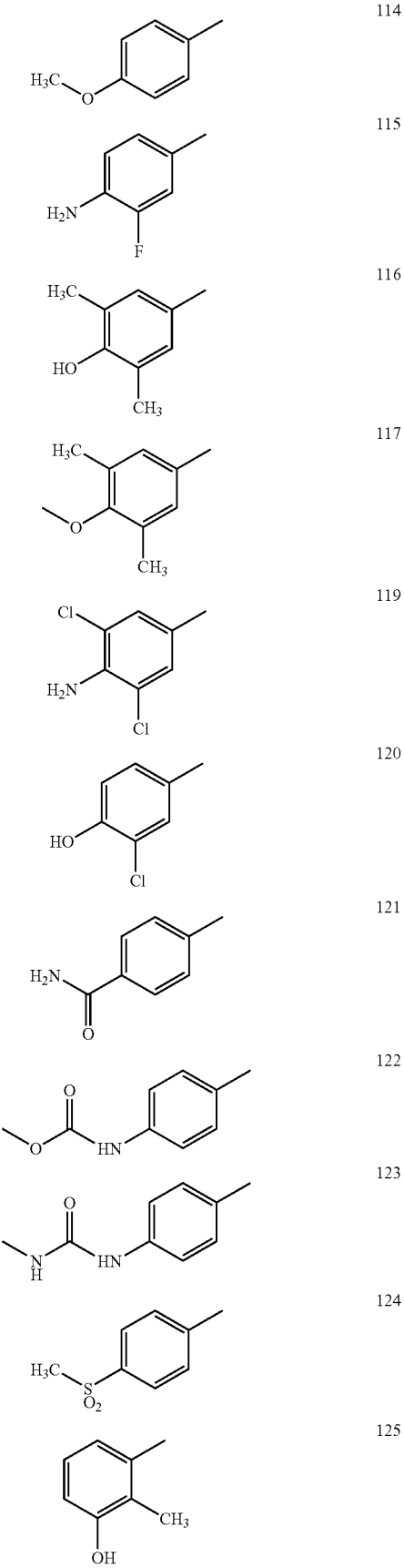

-continued
| | |
|---|---|
| 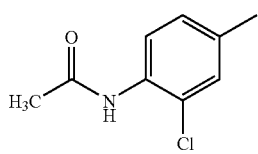 | 126 |
| 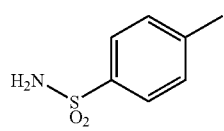 | 127 |
| 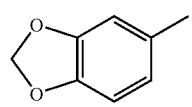 | 128 |
| 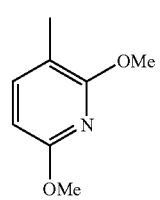 | 129 |
| 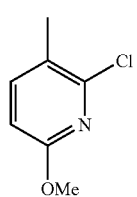 | 130 |
| 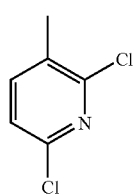 | 131 |
| 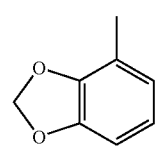 | 132 |
| 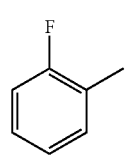 | 133 |
| 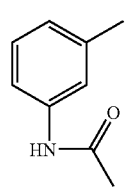 | 134 |
| 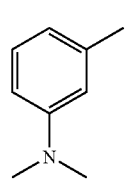 | 135 |
-continued
| | |
|---|---|
| 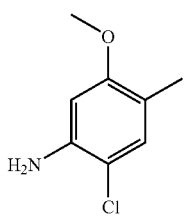 | 136 |
| 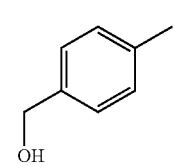 | 137 |
| 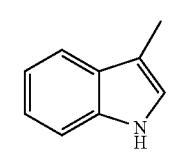 | 138 |
| 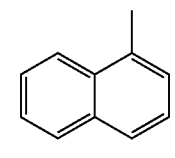 | 139 |
| 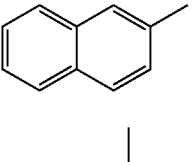 | 140 |
| 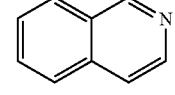 | 141 |
| 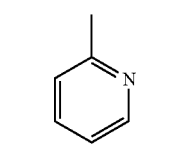 | 142 |
| 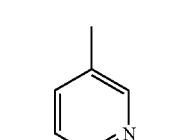 | 143 |
| $C_{1-12}$ Alkyl | 144 |
| 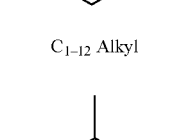 | 145 |
| 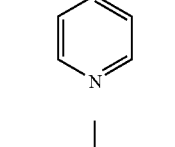 | 145 |
| 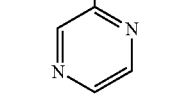 | 146 |

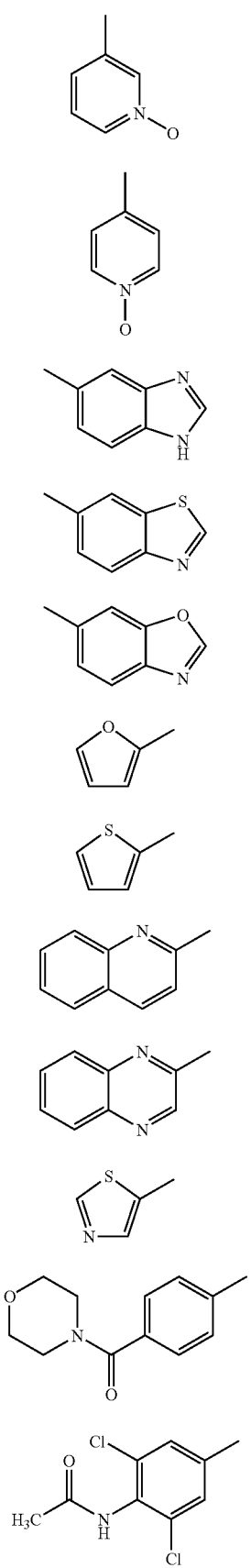
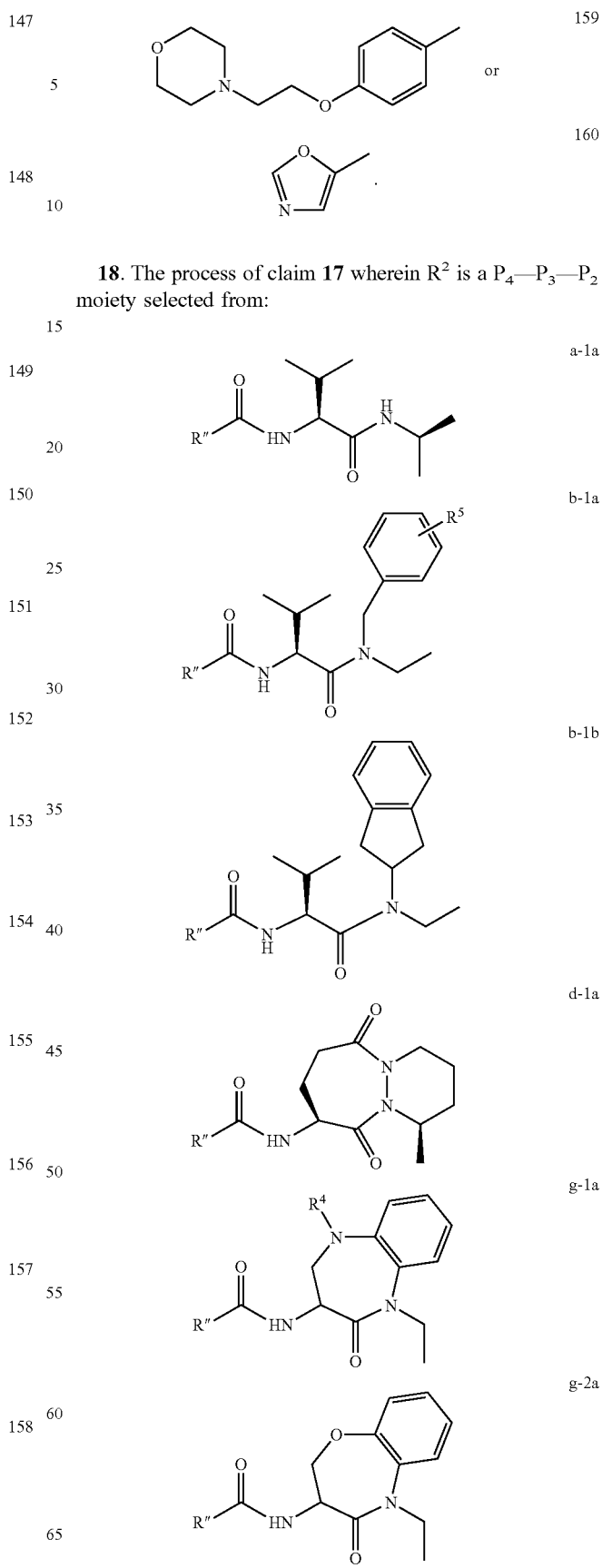
18. The process of claim 17 wherein $R^2$ is a $P_4$—$P_3$—$P_2$ moiety selected from:

-continued

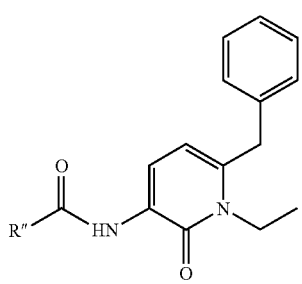 o-2a

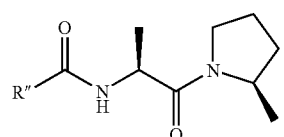 c-7a

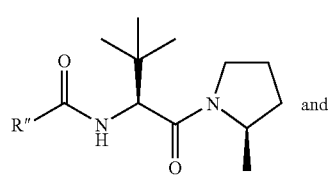 c-1a and

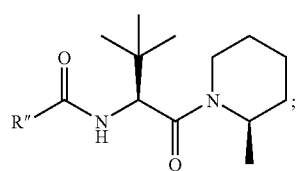 c-6a;

wherein R″ is:

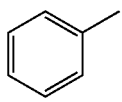 100

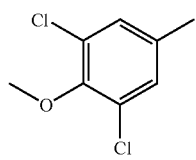 105

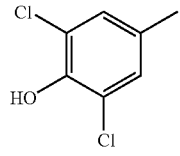 107

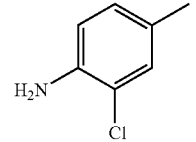 108

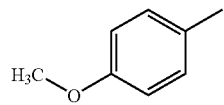 114

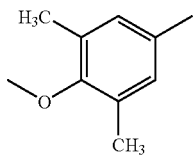 117

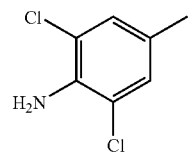 119

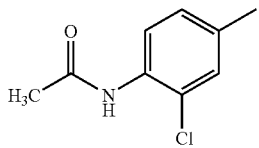 126

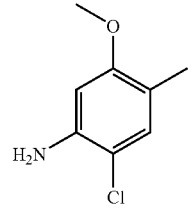 136

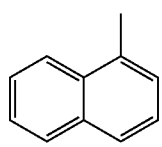 139

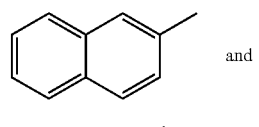 140 and

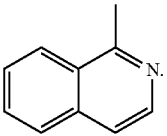 141

19. The process of claim 14 wherein $R^1$ is methyl, ethyl, propyl, 2-propyl, butyl, pentyl, hexyl, 4-methylpentyl, 2-methylpropyl, cyclopentyl, cyclohexyl, cyclopentylmethyl, cyclohexylmethyl, phenylethyl, phenylpropyl, phenylbutyl, (d)-menthyl, (l)-menthyl, 1-adamantyl, 2-adamantyl, 1-indanyl, 2-indanyl, bornyl, 3-tetrahydrofuranyl, benzyl, α-methylbenzyl, 4-chlorobenzyl, 4-fluorobenzyl, 4-methylbenzyl, 4-(2-propyl)benzyl, or 4-trifluoromethylbenzyl.

20. The process of claim 14 wherein $R^1$ is ethyl or an optionally substituted benzyl.

21. The process of claim 20 wherein $R^1$ is ethyl or benzyl.

22. The process of claim 13 or 14 wherein $N_3$—Y is selected from $LiN_3$, $NaN_3$, $TMS-N_3$, or $EtAlN_3$.

23. The process of claim 13 or 14 which proceeds through the aminolactone IX.

24. The process of claim 13 or 14 which proceeds through the iminophosphorane XI.

25. A process for making a compound of formula I:

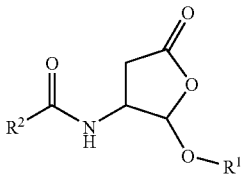

wherein $R^1$ is an optionally substituted group selected from an aliphatic group, aralkyl group, heterocyclylalkyl group or aryl group, and $R^2$ is an organic radical, said process comprising the steps of:

(a) providing a butenolactone VII:

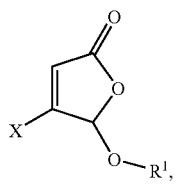

wherein X is chloro, bromo or iodo;

(b) treating VII with an azide $N_3$—Y, where Y is a silyl group or a counterion, to form an azidobutenolactone VIII:

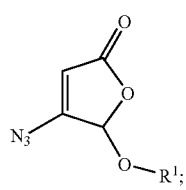

(c) converting VIII to an aminobutenolactone IX:

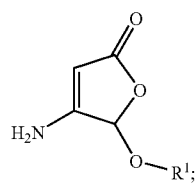

(d) reducing the rang double bond of IX to provide the aminolactone IV:

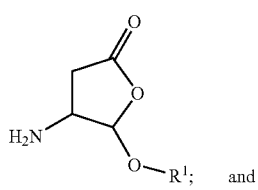

and (e) coupling IV with $R^2COOH$, or a reactive equivalent thereof, to form I.

26. The process of claim 25 wherein $R^2$ is a $P_4$—$P_3$—$P_2$ moiety of a caspase inhibitor, or portion thereof.

27. A compound of formula III or VIII:

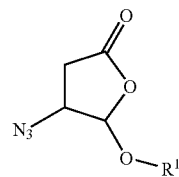

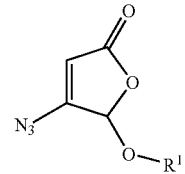

wherein $R^1$ is selected from an optionally substituted aliphatic group, aralkyl group or aryl group.

28. The compound of claim 27 wherein $R^1$ is methyl, ethyl, propyl, 2-propyl, butyl, pentyl, hexyl, 4-methylpentyl, 2-methylpropyl, cyclopentyl, cyclohexyl, cyclopentylmethyl, cyclohexylmethyl, phenylethyl, phenylpropyl, phenylbutyl, (d)-menthyl, (l)-menthyl, 1-adamantyl, 2-adamantyl, 1-indanyl, 2-indanyl, bornyl, 3-tetrahydrofuranyl, benzyl, α-methylbenzyl, 4-chlorobenzyl, 4-fluorobenzyl, 4-methylbenzyl, 4-(2-propyl)benzyl, or 4-trifluoromethylbenzyl.

29. The compound of claim 27 wherein $R^1$ is ethyl or an optionally substituted benzyl.

30. The compound of claim 29 wherein $R^1$ is ethyl or benzyl.

31. A compound of formula V or IX:

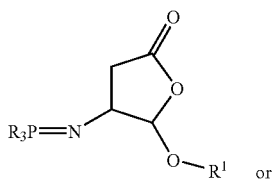

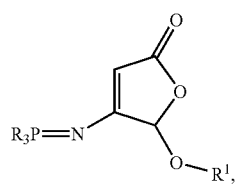

wherein $R^1$ is selected from an optionally substituted aliphatic group, aralkyl group or aryl group and R is derived from a phosphine or a phosphinite reducing agent.

32. The compound of claim 31 wherein $R^1$ is methyl, ethyl, propyl, 2-propyl, butyl, pentyl, hexyl, 4-methylpentyl, 2-methylpropyl, cyclopentyl, cyclohexyl, cyclopentylmethyl, cyclohexylmethyl, phenylethyl, phenylpropyl, phenylbutyl, (d)-menthyl, (l)-menthyl, 1-adamantyl, 2-adamantyl, 1-indanyl, 2-indanyl, bornyl, 3-tetrahydrofuranyl, benzyl, α-methylbenzyl, 4-chlorobenzyl, 4-fluorobenzyl, 4-methylbenzyl, 4-(2-propyl)benzyl, or 4-trifluoromethylbenzyl.

33. The compound of claim 31 wherein $R^1$ is ethyl or an optionally substituted benzyl.

34. The compound of claim 33 wherein $R^1$ is ethyl or benzyl.

35. The process of claim 4 or claim 16 where $R^2$ is RCO, where R is 1-naphthyl, 2-naphthyl, 1-isoquinolinyl, or:

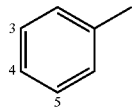

wherein positions 3 and 5 are independently and optionally substituted by halogen or $C_{1-3}$ alkyl, and position 4 is optionally substituted by amino, acetamido, hydroxy, or methoxy.

36. The process of any one of claims 1, 13, or 31, where $R^2$ is:

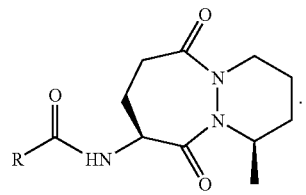

d-1a

37. The process of claim 36 wherein R is:

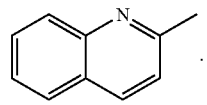

38. The process of any one of claims 1, 13, or 31, where $R^2$ is:

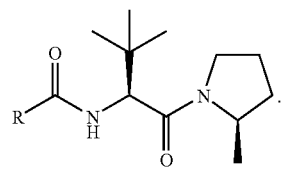

c-1a

39. The process of claim 38 where R is:

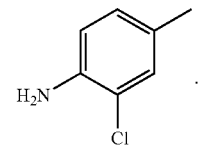

* * * * *